United States Patent
Endo et al.

(10) Patent No.: US 10,720,584 B2
(45) Date of Patent: *Jul. 21, 2020

(54) CHARGE-TRANSPORTING VARNISH, AND ORGANIC ELECTROLUMINESCENT ELEMENT

(71) Applicant: NISSAN CHEMICAL INDUSTRIES, LTD., Tokyo (JP)

(72) Inventors: Toshiyuki Endo, Funabashi (JP); Taichi Nakazawa, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 53 days.

This patent is subject to a terminal disclaimer.

(21) Appl. No.: 15/576,588

(22) PCT Filed: May 25, 2016

(86) PCT No.: PCT/JP2016/065379
§ 371 (c)(1),
(2) Date: Nov. 22, 2017

(87) PCT Pub. No.: WO2016/190326
PCT Pub. Date: Dec. 1, 2016

(65) Prior Publication Data
US 2018/0151805 A1 May 31, 2018

(30) Foreign Application Priority Data
May 27, 2015 (JP) ................. 2015-107093

(51) Int. Cl.
| | |
|---|---|
| H01B 1/12 | (2006.01) |
| H01L 51/00 | (2006.01) |
| C07C 231/12 | (2006.01) |
| C07C 233/80 | (2006.01) |
| C09K 11/06 | (2006.01) |
| C07C 209/10 | (2006.01) |
| C07C 211/55 | (2006.01) |
| C07C 231/02 | (2006.01) |
| C07C 231/14 | (2006.01) |

(Continued)

(52) U.S. Cl.
CPC ........ *H01L 51/0035* (2013.01); *C07C 209/10* (2013.01); *C07C 211/55* (2013.01); *C07C 231/02* (2013.01); *C07C 231/12* (2013.01); *C07C 231/14* (2013.01); *C07C 233/80* (2013.01); *C08G 73/0266* (2013.01); *C09D 5/24* (2013.01); *C09D 179/02* (2013.01); *C09K 11/06* (2013.01); *H01B 1/12* (2013.01); *H01L 51/0043* (2013.01); *H01L 51/0059* (2013.01); *C07B 61/00* (2013.01); *H01L 51/5088* (2013.01)

(58) Field of Classification Search
CPC ..... C07B 61/00; C07C 209/10; C07C 211/55; C07C 231/02; C07C 231/12; C07C 231/14; C07C 233/80; C08G 73/0266; C09K 11/06; H01L 51/0035; H01L 51/0043; H01L 51/0059; H01L 51/5088; C09D 179/02; C09D 5/24; H01B 1/12
See application file for complete search history.

(56) References Cited

U.S. PATENT DOCUMENTS 10,301,484 B2 * 5/2019 Higashi ................ C09D 5/24
2008/0029742 A1 2/2008 Yoshimoto et al.
(Continued)

FOREIGN PATENT DOCUMENTS

| CN | 103254432 A | 8/2013 |
|---|---|---|
| EP | 3 121 163 A1 | 1/2017 |

(Continued)

OTHER PUBLICATIONS

Office Action dated Jun. 12, 2018, in Korean Patent Application No. 10-2017-7008905.

(Continued)

*Primary Examiner* — Mark Kopec
*Assistant Examiner* — Jaison P Thomas
(74) *Attorney, Agent, or Firm* — Birch, Stewart, Kolasch & Birch, LLP

(57) ABSTRACT

Provided are: a charge-transporting varnish that contains a charge-transporting substance comprising an oligoaniline derivative represented by formula (1), a charge transporting substance that does not contain fluorine atoms, and an organic solvent; and an organic electroluminescent element including a thin film obtained from the varnish.

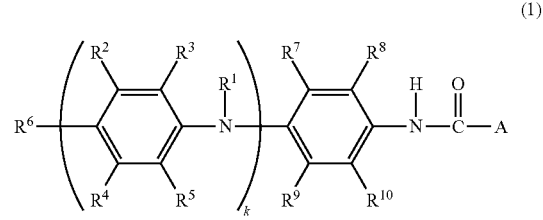

(1)

(In the formula: $R^1$ represents a hydrogen atom or an alkyl group that may be substituted; $R^2$ to $R^{10}$ each independently represent a hydrogen atom, a halogen atom, a nitro group, a cyano group, or an alkyl group, alkenyl group, alkynyl group, aryl group or heteroaryl group that may be substituted; A represents a prescribed fluorine atom-containing substituent; and k represents an integer from 1 to 20.)

10 Claims, No Drawings

(51) Int. Cl.
*C08G 73/02* (2006.01)
*C09D 5/24* (2006.01)
*C09D 179/02* (2006.01)
*C07B 61/00* (2006.01)
*H01L 51/50* (2006.01)

(56) References Cited

U.S. PATENT DOCUMENTS

| | | | |
|---|---|---|---|
| 2010/0159279 A1 | 6/2010 | Kato et al. | |
| 2010/0230639 A1 | 9/2010 | Yamada et al. | |
| 2013/0085133 A1* | 4/2013 | Severson | A61K 31/405 |
| | | | 514/214.02 |
| 2016/0005972 A1 | 1/2016 | Otani | |
| 2016/0248017 A1 | 8/2016 | Otani | |

FOREIGN PATENT DOCUMENTS

| | | |
|---|---|---|
| TW | 201502155 A | 1/2015 |
| WO | WO 2006/025342 A1 | 3/2006 |
| WO | WO 2008/032616 A1 | 3/2008 |
| WO | WO 2008/129947 A1 | 10/2008 |
| WO | WO 2010/058777 A1 | 5/2010 |
| WO | WO 2014/132917 A1 | 9/2014 |
| WO | WO 2014/148415 A1 | 9/2014 |
| WO | WO 2015/050057 A1 | 4/2015 |
| WO | WO 2015/141585 A1 | 9/2015 |
| WO | WO-2016117521 A1 * | 7/2016 ............... C09D 5/24 |

OTHER PUBLICATIONS

Taiwanese Office Action and Search Report dated Sep. 30, 2017, for corresponding Taiwanese Application No. 105116456.
Chao et al., "Novel Electroactive Poly(arylene ether sulfone) Copolymers Containing Pendant Oligoaniline Groups: Synthesis and Properties", Journal of Polymer Science Part A: Polymer Chemistry, vol. 49, 2011, pp. 1605-1614.
International Search Report (PCT/ISA/210) issued in PCT/JP2016/065379, dated Aug. 30, 2016.
McCoy et al., "Potential-Dependent Nucleophilicity of Polyaniline", J. Am. Chem. Soc., vol. 117, No. 26, 1995, pp. 6934-6943.
Written Opinion (PCT/ISA/237) issued in PCT/JP2016/065379, dated Aug. 30, 2016.
Zhang et al., "Electroactive Polymer with Oligoanilines in the Main Chain: Synthesis, Characterization and Dielectric Properties", Macromolecular Chemistry and Physics, vol. 210, No. 20, 2009, pp. 1739-1745.

* cited by examiner

CHARGE-TRANSPORTING VARNISH, AND ORGANIC ELECTROLUMINESCENT ELEMENT

TECHNICAL FIELD

The present invention relates to a charge-transporting varnish and an organic electroluminescent (EL) device.

BACKGROUND ART

Organic EL devices have charge-transporting thin films formed from organic compounds which function as light emitting layers and charge-injecting layers. Particularly, a hole injection layer is responsible for transferring charges between an anode and a hole-transporting layer or a light emitting layer, and thus plays an important role in organic EL devices to work at a low voltage and achieve a high luminance.

The hole injection layer is produced by either dry processes (typified by vapor deposition) or wet processes (typified by spin coating). Comparing these processes, wet processes are superior to the dry process in ability to efficiently produce a flat thin film with a large area. Thus, there is an increasing demand for the hole injection layer that can be produced by wet processes in view of the fact that organic EL displays are evolving into one with a larger screen area than before.

With the above in mind, the present inventors have been engaged in the development of various charge-transporting materials which are applicable to a variety of wet processes and which give rise to outstanding thin films for hole injection layers of organic EL devices. The present inventors also have developed new compounds highly dissolvable in organic solvents and new charge transporting varnishes. (See Patent Documents 1 to 4.)

PRIOR ART DOCUMENTS

Patent Documents

Patent Document 1: WO 2008/032616
Patent Document 2: WO 2008/129947
Patent Document 3: WO 2006/025342
Patent Document 4: WO 2010/058777

SUMMARY OF THE INVENTION

Problems to be Solved by the Invention

It is an object of the invention to provide a charge-transporting varnish and an organic EL device which has a thin film formed from the varnish. The varnish gives rise to a thin film with outstanding characteristic properties for use as hole injection layers of organic EL devices. This object is the same as that described in the above-mentioned Patent Documents.

Means for Solving the Problems

As the result of extensive investigations to achieve the above object, the present inventors found that a thin film highly capable of charge transportation can be obtained from a specific charge-transporting varnish and the thin film can be applied to the hole injection layer of an organic EL device with outstanding electric characteristics. The charge-transporting varnish includes a charge-transporting substance which is a specific oligoaniline derivative containing fluorine atoms, a charge-transporting substance free of fluorine atoms, an organic solvent, and an optional dopant. The above findings led to the invention.

Thus, the present invention provides a charge-transporting varnish and an organic EL device which are described below.

1. A charge-transporting varnish including a charge-transporting substance of a fluorine-containing oligoaniline derivative represented by the formula (1) below, a fluorine-free charge-transporting substance, and an organic solvent

[Chemical Formula 1]

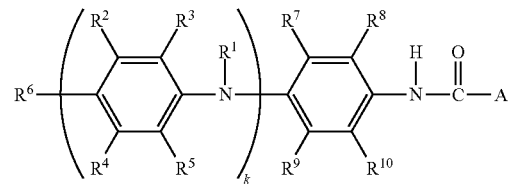

(1)

wherein $R^1$ is a hydrogen atom or alkyl group having 1 to 20 carbon atoms which may be substituted with Z, Z is a halogen atom, nitro group, cyano group, aldehyde group, hydroxy group, thiol group, sulfonic acid group, carboxyl group, an aryl group having 6 to 20 carbon atoms and which may be substituted with Z', or heteroaryl group having 2 to 20 carbon atoms which may be substituted with Z', and Z' is a halogen atom, nitro group, cyano group, aldehyde group, hydroxy group, thiol group, sulfonic acid group, or carboxyl group;

$R^2$ to $R^{10}$ are independently a hydrogen atom, halogen atom, nitro group, cyano group, or alkyl group having 1 to 20 carbon atoms, alkenyl group having 2 to 20 carbon atoms, alkynyl group having 2 to 20 carbon atoms, aryl group having 6 to 20 carbon atoms, or heteroaryl group having 2 to 20 carbon atoms which may be substituted with a halogen atom;

letter A is
a fluoroalkyl group having 1 to 20 carbon atoms, fluorocycloalkyl group having 3 to 20 carbon atoms, fluorobicycloalkyl group having 4 to 20 carbon atoms, fluoroalkenyl group having 2 to 20 carbon atoms or fluroalkynyl group having 2 to 20 carbon atoms which may be substituted with a cyano group, chlorine atom, bromine atom, iodine atom, nitro group or fluoroalkoxy group having 1 to 20 carbon atoms, a fluoroaryl group having 6 to 20 carbon atoms which may be substituted with a cyano group, chlorine atom, bromine atom, iodine atom, nitro group, alkyl group having 1 to 20 carbon atoms, fluoroalkyl group having 1 to 20 carbon atoms or fluoroalkoxy group having 1 to 20 carbon atoms, an aryl group having 6 to 20 carbon atoms which is substituted with a fluoroalkyl group having 1 to 20 carbon atoms, fluorocycloalkyl group having 3 to 20 carbon atoms, fluorobicycloalkyl group having 4 to 20 carbon atoms, fluoroalkenyl group having 2 to 20 carbon atoms or fluoroalkynyl group having 2 to 20 carbon atoms, and may be substituted with a cyano group, halogen atom or fluoroalkoxy group having 1 to 20 carbon atoms, a fluoroaralkyl group having 7 to 20 carbon atoms which may be substituted with a cyano group, chlorine atom, bromine atom, iodine atom, nitro group, fluoroalkoxy group having 1 to 20 carbon atoms, fluoroalkyl group having 1 to 20 carbon atoms, fluorocycloalkyl group having 3 to 20 carbon atoms, fluorobicycloalkyl group having 4 to 20 carbon atoms, fluoroalkenyl group having 2 to 20 carbon atoms or fluoroalkynyl group having 2 to 20 carbon atoms, or an aralkyl group having 7 to 20 carbon atoms which is substituted with a fluoroalkyl group having 1 to 20 carbon atoms, fluorocycloalkyl group having 3 to 20 carbon atoms, fluorobicycloalkyl group having 4 to 20 carbon atoms, fluoroalkenyl group having 2 to 20 carbon atoms or fluoroalkynyl group having 2 to 20 carbon atoms, and may be substituted with a cyano group, halogen atom or fluoroalkoxy group having 1 to 20 carbon atoms; and letter k is an integer of 1 to 20.

2. The charge-transporting varnish of 1 above, wherein letter A is a fluoroalkyl group having 1 to 20 carbon atoms which may be substituted with a cyano group, chlorine atom, bromine atom, iodine atom, nitro group or fluoroalkoxy group having 1 to 20 carbon atoms; a fluoroaryl group having 6 to 20 carbon atoms which may be substituted with a cyano group, chlorine atom, bromine atom, iodine atom, nitro group, alkyl group having 1 to 20 carbon atoms, fluoroalkyl group having 1 to 20 carbon atoms or fluoroalkoxy group having 1 to 20 carbon atoms; or an aryl group having 6 to 20 carbon atoms is substituted with a fluoroalkyl group having 1 to 20 carbon atoms, fluorocycloalkyl group having 3 to 20 carbon atoms, fluorobicycloalkyl group having 4 to 20 carbon atoms, fluoroalkenyl group having 2 to 20 carbon atoms or fluoroalkynyl group having 2 to 20 carbon atoms, and may be substituted with a cyano group, halogen atom, or fluoroalkoxy group having 1 to 20 carbon atoms.

3. The charge-transporting varnish of 2 above, wherein letter A is a phenyl group which is substituted with at least 3 fluorine atoms, and may be substituted with a cyano group, chlorine atom, bromine atom, iodine atom, nitro group, alkyl group having 1 to 20 carbon atoms, fluoroalkyl group having 1 to 20 carbon atoms or fluoroalkoxy group having 1 to 20 carbon atoms; or a phenyl group which is substituted with a fluorocycloalkyl group having 3 to 20 carbon atoms, fluorobicycloalkyl group having 4 to 20 carbon atoms, fluoroalkenyl group having 2 to 20 carbon atoms, or fluoroalkynyl group having 2 to 20 carbon atoms, and may be substituted with a cyano group, halogen atom, or fluoroalkoxy group having 1 to 20 carbon atoms.

4. The charge-transporting varnish of any one of 1 to 3 above, wherein $R^1$ is a hydrogen atom.

5. The charge-transporting varnish of any one of 1 to 4 above, wherein $R^2$ to $R^{10}$ are a hydrogen atom.

6. The charge-transporting varnish of any one of 1 to 5 above, wherein letter k is an integer of 2 to 10.

7. The charge-transporting varnish of any one of 1 to 6 above, wherein the fluorine-free charge-transporting substance is a compound represented by the formula (4) below:

wherein $X^1$ is $-NY^1-$, $-O-$, $-S-$, $-(CR^{17}R^{18})_L-$, or a single bond, except that it is $-NY^1-$ when m or n is 0;

$Y^1$ is independently a hydrogen atom, alkyl group having 1 to 20 carbon atoms, alkenyl group having 2 to 20 carbon atoms or alkynyl group having 2 to 20 carbon atoms which may be substituted with $Z^{11}$, or aryl group having 6 to 20 carbon atoms or heteroaryl group having 2 to 20 carbon atoms which may be substituted with $Z^{12}$;

$R^{17}$ and $R^{18}$ are independently a hydrogen atom, halogen atom, nitro group, cyano group, amino group, aldehyde group, hydroxy group, thiol group, sulfonic acid group, carboxyl group, or alkyl group having 1 to 20 carbon atoms, alkenyl group having 2 to 20 carbon atoms or alkynyl group having 2 to 20 carbon atoms which may be substituted with $Z^{11}$, or aryl group having 6 to 20 carbon atoms or heteroaryl group having 2 to 20 carbon atoms which may be substituted with $Z^{12}$, or $-NHY^2$, $-NY^3Y^4$, $-C(O)Y^5$, $-OY^6$, $-SY^7$, $-SO_3Y^8$, $-C(O)OY^9$, $-OC(O)Y^{10}$, $-C(O)NHY^{11}$ or $-C(O)NY^{12}Y^{13}$;

$R^{11}$ to $R^{16}$ are independently a hydrogen atom, halogen atom, nitro group, cyano group, amino group, aldehyde group, hydroxy group, thiol group, sulfonic acid group, carboxyl group, or alkyl group having 1 to 20 carbon atoms, alkenyl group having 2 to 20 carbon atoms or alkynyl group having 2 to 20 carbon atoms which may be substituted with $Z^{11}$, or aryl group having 6 to 20 carbon atoms, or heteroaryl group having 2 to 20 carbon atoms which may be substituted with $Z^{12}$, or $-NHY^2$, $-NY^3Y^4$, $-C(O)Y^5$, $-OY^6$, $-SY^7$, $-SO_3Y^8$, $-C(O)OY^9$, $-OC(O)Y^{10}$, $-C(O)NHY^{11}$ or $-C(O)NY^{12}Y^{13}$;

$Y^2$ to $Y^{13}$ are independently alkyl group having 1 to 20 carbon atoms, alkenyl group having 2 to 20 carbon atoms or alkynyl group having 2 to 20 carbon atoms which may be substituted with $Z^{11}$, or aryl group having 6 to 20 carbon atoms or heteroaryl group having 2 to 20 carbon atoms which may be substituted with $Z^{12}$;

$Z^{11}$ is a halogen atom, nitro group, cyano group, amino group, aldehyde group, hydroxy group, thiol group, sulfonic acid group, carboxyl group, or aryl group having 6 to 20 carbon atoms or heteroaryl group having 2 to 20 carbon atoms which has an optional substituent of $Z^{13}$;

$Z^{12}$ is a halogen atom, nitro group, cyano group, amino group, aldehyde group, hydroxy group, thiol group, sulfonic acid group, carboxyl group, or alkyl group having 1 to 20 carbon atoms, alkenyl group having 2 to 20 carbon atoms or alkynyl group having 2 to 20 carbon atoms which may be substituted with $Z^{13}$;

$Z^{13}$ is a halogen atom, nitro group, cyano group, amino group, aldehyde group, hydroxy group, thiol group, sulfonic acid group, or carboxyl group; and letters of m and n are independently an integer at least 0, such that $1 \leq m+n \leq 20$.

[Chemical Formula 2]

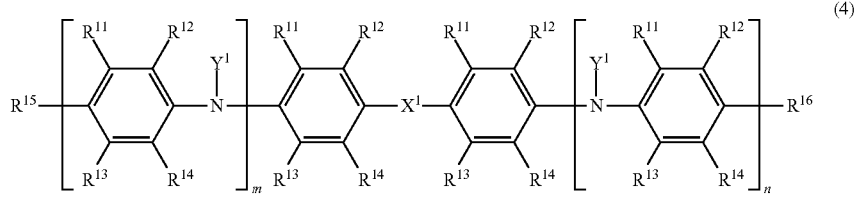

(4)

8. The charge-transporting varnish of any one of 1 to 7 above, further including a dopant.
9. A charge-transporting thin film which is produced from the charge-transporting varnish of any one of 1 to 8 above.
10. An organic EL device comprising the charge-transporting thin film of 9 above.
11. A method for producing a fluorine-containing oligoaniline derivative represented by the formula (1) below, the method including reacting an amine compound represented by the formula (2B) with a fluorine-containing compound represented by the formula (3B) or (3B') in the presence of a base

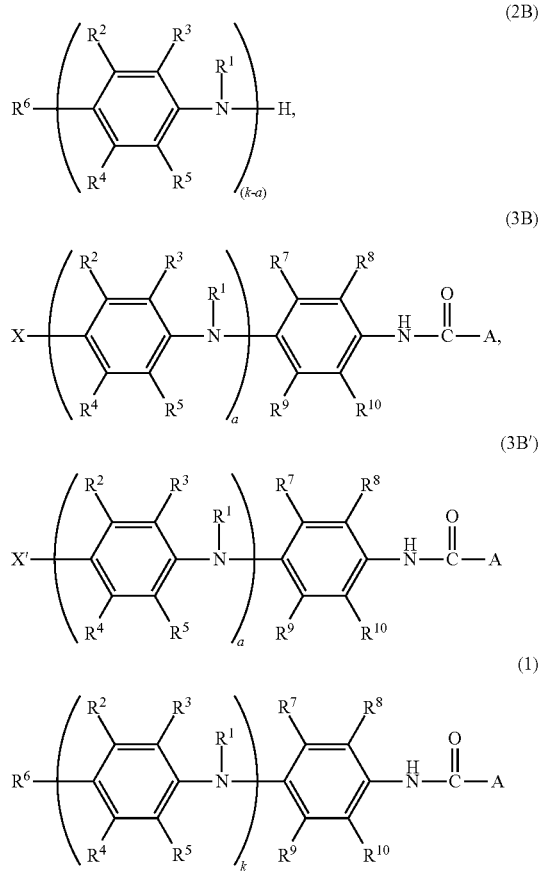

wherein $R^1$ to $R^{10}$ and letters A and k are as defined above, X is a halogen atom, X' is a pseudo halogen group; and letter a is an integer of 0 to 19, with k>a.

Advantageous Effects of the Invention

The charge-transporting varnish of the invention gives a thin film highly capable of transporting charges, which is suitable for electronic devices such as organic EL devices. This thin film is particularly useful as a hole-injecting layer for organic EL devices which are intended to have outstanding luminance characteristics.

The charge-transporting varnish of the invention can be made consistently into a thin film with outstanding charge-transporting properties by wet processes, such as spin coating and slit coating, which is suitable for the production of large-area thin film. Consequently, it will meet the need in the field of organic EL devices which have remarkably advanced recently.

EMBODIMENT FOR CARRYING OUT THE INVENTION

[Charge-Transporting Substance Based on Fluorine-Containing Oligoaniline Derivative]

The charge-transporting varnish of the invention contains the charge-transporting substance based on the fluorine-containing oligoaniline derivative represented by the formula (1) below. Incidentally, the term "charge-transporting" is synonymous with "conducting" or "hole-transporting." The charge transporting varnish of the invention may be one which is capable of transporting charges by itself or one which gives a solid film capable of transporting charges.

[Chemical Formula 4]

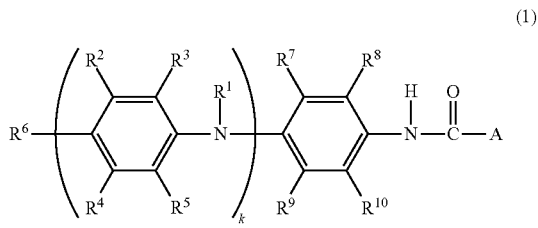

In the formula, $R^1$ is a hydrogen atom or alkyl group having 1 to 20 carbon atoms and may be substituted with Z. Z is a halogen atom, nitro group, cyano group, aldehyde group, hydroxy group, thiol group, sulfonic acid group, carboxyl group, an aryl group having 6 to 20 carbon atoms which may be substituted with Z', or heteroaryl group having 2 to 20 carbon atoms which may be substituted with Z'. Z' is a halogen atom, nitro group, cyano group, aldehyde group, hydroxy group, thiol group, sulfonic acid group, or carboxyl group.

$R^2$ to $R^{10}$ are independently a hydrogen atom, halogen atom, nitro group, cyano group, or alkyl group having 1 to 20 carbon atoms, alkenyl group having 2 to 20 carbon atoms, alkynyl group having 2 to 20 carbon atoms, aryl group having 6 to 20 carbon atoms or heteroaryl group having 2 to 20 carbon atoms which may be substituted with halogen atom.

Examples of the halogen atom include, for example, fluorine atom, chlorine atom, bromine atom, and iodine atom.

The alkyl group having 1 to 20 carbon atoms may be linear, branched, or cyclic. Examples of the linear or branched alkyl group having 1 to 20 carbon atoms include, for example, a methyl group, ethyl group, n-propyl group, isopropyl group, n-butyl group, isobutyl group, s-butyl group, t-butyl group, n-pentyl group, n-hexyl group, n-heptyl group, n-octyl group, n-nonyl group, and n-decyl group. Examples of the cyclic alkyl group having 3 to 20 carbon atoms include, for example, cyclopropyl group, cyclobutyl group, cyclopentyl group, cyclohexyl group, cycloheptyl group, cyclooctyl group, cyclononyl group, cyclodecyl group, bicyclobutyl group, bicyclopentyl group, bicyclohexyl group, bicycloheptyl group, bicyclooctyl group, bicyclononyl group, and bicyclodecyl group.

The alkenyl group having 2 to 20 carbon atoms may be linear, branched, or cyclic. Examples of the alkenyl group having 2 to 20 carbon atoms include, for example, an ethenyl group, n-1-propenyl group, n-2-propenyl group, 1-methylethenyl group, n-1-butenyl group, n-2-butenyl group, n-3-butenyl group, 2-methyl-1-propyenyl group, 2-methyl-2-propyenyl group, 1-ethylethenyl group, 1-methyl-1-propenyl group, 1-methyl-2-propenyl group, n-1-pentenyl group, n-1-decenyl group, and n-1-eicosenyl group.

The alkynyl group having 2 to 20 carbon atoms may be linear, branched, or cyclic. Examples of the alkynyl group having 2 to 20 carbon atoms include, for example, an ethynyl group, n-1-propynyl group, n-2-propynyl group, n-1-butyryl group, n-2-butynyl group, n-3-butynyl group, 1-methyl-2-propynyl group, n-1-pentynyl group, n-2-pentynyl group, n-3-pentynyl group, n-4-pentynyl group, 1-methyl-n-butynyl group, 2-methyl-n-butynyl group, 3-methyl-n-butynyl group, 1,1-dimethyl-n-propynyl group, n-1-hexynyl group, n-1-decynyl group, n-1-pentadecynyl group, and n-1-eicosynyl group.

Examples of the aryl group having 6 to 20 carbon atoms include, for example, a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, and 9-phenanthryl group.

Examples of the heteroaryl group having 2 to 20 carbon atoms include, for example, a 2-thienyl group, 3-thienyl group, 2-furanyl group, 3-furanyl group, 2-oxazolyl group, 4-oxazolyl group, 5-oxazolyl group, 3-isooxazolyl group, 4-isooxazolyl group, 5-isooxazolyl group, 2-thiazolyl group, 4-thiazolyl group, 5-thiazolyl group, 3-isothiazolyl group, 4-isothiazolyl group, 5-isothiazolyl group, 2-imidazolyl group, 4-imidazolyl group, 2-pyridyl group, 3-pyridyl group, and 4-pyridyl group.

$R^1$ should preferably be a hydrogen atom or an alkyl group having 1 to 10 carbon atoms which may be substituted with Z, more preferably a hydrogen atom or an alkyl group having 1 to 4 carbon atoms which may be substituted with Z, and most preferably a hydrogen atom, from the standpoint of the solubility of the oligoaniline derivative in organic solvents. Incidentally, each of $R^1$ may be identical or different.

In the case where $R^1$ is a hydrogen atom, the oligoaniline derivative indicates outstanding charge-transporting performance when it is combined with a dopant which is a protonic acid such as arylsulfonic acid and heteropoly acid.

$R^2$ to $R^{10}$ should preferably be a hydrogen atom, halogen atom, nitro group, cyano group, or an alkyl group having 1 to 10 carbon atoms which may be substituted with halogen atom, and more preferably a hydrogen atom, halogen atom, or an alkyl group having 1 to 4 carbon atoms which may be substituted with halogen atom, from the standpoint of the solubility of the oligoaniline derivative in organic solvents. $R^2$ to $R^{10}$ should most preferably be a hydrogen atom from the stand point of the oligoaniline derivative having good solubility in organic solvents and good charge-transporting performance. Incidentally, each of $R^2$ to $R^{10}$ may be identical or different.

In formula (1), letter A is a fluoroalkyl group having 1 to 20 carbon atoms, fluorocycloalkyl group having 3 to 20 carbon atoms, fluorobicycloalkyl group having 4 to 20 carbon atoms, fluoroalkenyl group having 2 to 20 carbon atoms or fluoalkynyl group having 2 to 20 carbon atoms which may be substituted with a cyano group, chlorine atom, bromine atom, iodine atom, nitro group or fluoroalkoxy group having 1 to 20 carbon atoms; a fluoroaryl group having 6 to 20 carbon atoms which may be substituted with a cyano group, chlorine atom, bromine atom, iodine atom, nitro group, alkyl group having 1 to 20 carbon atoms, fluoroalkyl group having 1 to 20 carbon atoms or fluoroalkoxy group having 1 to 20 carbon atoms; an aryl group having 6 to 20 carbon atoms which is substituted with a fluoroalkyl group having 1 to 20 carbon atoms, fluorocycloalkyl group having 3 to 20 carbon atoms, fluorobicycloalkyl group having 4 to 20 carbon atoms, fluoroalkenyl group having 2 to 20 carbon atoms or fluoroalkynyl group having 2 to 20 carbon atoms and may be substituted with a cyano group, halogen atom or fluoroalkoxy group having 1 to 20 carbon atoms; a fluoroaralkyl group having 7 to 20 carbon atoms which may be substituted with a cyano group, chlorine atom, bromine atom, iodine atom, nitro group, fluoroalkoxy group having 1 to 20 carbon atoms, fluoroalkyl group having 1 to 20 carbon atoms, fluorocycloalkyl group having 3 to 20 carbon atoms, fluorobicycloalkyl group having 4 to 20 carbon atoms, fluoroalkenyl group having 2 to 20 carbon atoms or fluoroalkynyl group having 2 to 20 carbon atoms; or an aralkyl group having 7 to 20 carbon atoms which is substituted with a fluoroalkyl group having 1 to 20 carbon atoms, fluorocycloalkyl group having 3 to 20 carbon atoms, fluorobicycloalkyl group having 4 to 20 carbon atoms, fluoroalkenyl group having 2 to 20 carbon atoms or fluoroalkynyl group having 2 to 20 carbon atoms, and may be substituted with a cyano group, halogen atom or fluoroalkoxy group having 1 to 20 carbon atoms.

The fluoroalkyl group mentioned above is not specifically restricted so long as it is a linear or branched alkyl group in which at least one hydrogen atom on a carbon atom is substituted with a fluorine atom. Examples of the fluoroalkyl group include, for example, a fluoromethyl group, difluoromethyl group, trifluoromethyl group, 1-fluoroethyl group, 2-fluoroethyl group, 1,2-difluoroethyl group, 1,1-difluoroethyl group, 2,2-difluoroethyl group, 1,1,2-trifluoroethyl group, 1,2,2-trifluoroethyl group, 2,2,2-trifluoroethyl group, 1,1,2,2-tetrafluoroethyl group, 1,2,2,2-tetrafluoroethyl group, 1,1,2,2,2-pentafluoroethyl group, 1-fluoropropyl group, 2-fluoropropyl group, 3-fluoropropyl group, 1,1-difluoropropyl group, 1,2-difluoropropyl group, 1,3-difluoropropyl group, 2,2-difluoropropyl group, 2,3-difluoropropyl group, 3,3-difluoropropyl group, 1,1,2-trifluoropropyl group, 1,1,3-trifluoropropyl group, 1,2,3-trifluoropropyl group, 1,3,3-trifluoropropyl group, 2,2,3-trifluoropropyl group, 2,3,3-trifluoropropyl group, 3,3,3-trifluoropropyl group, 1,1,2,2-tetrafluoropropyl group, 1,1,2,3-tetrafluoropropyl group, 1,2,2,3-tetrafluoropropyl group, 1,3,3,3-tetrafluoropropyl group, 2,2,3,3-tetrafluoropropyl group, 2,3,3,3-tetrafluoropropyl group, 1,1,2,2,3-pentafluoropropyl group, 1,2,2,3,3-pentafluoropropyl group, 1,1,3,3,3-pentafluoropropyl group, 1,2,3,3,3-pentafluoropropyl group, 2,2,3,3,3-pentafluoropropyl group, and heptafluoropropyl group.

The fluorocycloalkyl group mentioned above is not specifically restricted so long as it is a cycloalkyl group in which at least one hydrogen atom on a carbon atom is substituted with a fluorine atom. Examples of the fluorocycloalkyl group include, for example, a 1-fluorocyclopropyl group, 2-fluorocyclopropyl group, 2,2-difluorocyclopropyl group, 2,2,3,3-tetrafluorocyclopropyl group, pentafluorocyclopropyl group, 2,2-difluorocyclobutyl group, 2,2,3,3-tetrafluorocyclobutyl group, 2,2,3,3,4,4-hexafluorocyclobutyl group, heptafluorocyclobutyl group, 1 fluorocyclopentyl group, 3 fluorocyclopentyl group, 3,3 difluorocyclopentyl group, 3,3,4,4-tetrafluorocyclopentyl group, nonafluorocyclopentyl group, 1-fluorocyclohexyl group, 2-fluorocyclohexyl group, 4-fluorocyclohexyl group, 4,4-difluorocyclohexyl group, 2,2,3,3-tetrafluorocyclohexyl group, 2,3,4,5,6-pentafluorocyclohexyl group, and undecafluorocyclohexyl group.

The fluorobicycloalkyl group at least one hydrogen atom on a carbon atom is substituted with a fluorine atom. Examples of the fluorobicycloalkyl group include, for example, a 3-fluorobicyclo[1.1.0]butane-1-yl group, 2,2,4,4-tetrafluorobicyclo[1.1.0]butane-1-yl group, pentafluorobicyclo[1.1.0]butane-1-yl group, 3-fluorobicyclo[1.1.1]pentane-1-yl group, 2,2,4,4,5-pentafluorobicyclo[1.1.1]pentane-1-yl group, 2,2,4,4,5,5-hexafluorobicyclo[1.1.1]pentane-1-yl group, 5-fluorobicyclo[3.1.0]hexan-6-yl group, 6-fluorobicyclo[3.1.0]hexan-6-yl group, 6,6-difluorobicyclo[3.1.0]hexan-2-yl group, 2,2,3,3,5,5,6,6-octafluorobicyclo[2.2.0]hexan-1-yl group, 1-fluorobicyclo[2.2.1]heptane-2-yl group, 3-fluorobicyclo[2.2.1]heptane-2-yl group, 4-fluorobicyclo[2.2.1]heptane-1-yl group, 5-fluorobicyclo[3.1.1]heptane-1-yl group, 1,3,3,4,5,5,6,6,7,7-decafluorobicyclo[2.2.1]heptane-2-yl group, undecafluorobicyclo[2.2.1]heptane-2-yl group, 3-fluorobicyclo[2.2.2]octane-1-yl group, and 4-fluorobicyclo[2.2.2]octane-1-yl group.

The fluoroalkenyl group mentioned above is not specifically restricted so long as it is an alkenyl group in which at least one hydrogen atom on a carbon atom is substituted with a fluorine atom. Examples of the fluoroalkenyl group include, for example, 1-fluoroethenyl group, 2-fluoroethenyl group, 1,2-difluoroethenyl group, 1,2,2-trifluoroethenyl group, 2,3,3-trifluoro-1-propenyl group, 3,3,3-trifluoro-1-propenyl group, 2,3,3,3-tetrafluoro-1-propenyl group, pentafluoro-1-propenyl group, 1-fluoro-2-propenyl group, 1,1-difluoro-2-propenyl group, 2,3-difluoro-2-propenyl group, 3,3-difluoro-2-propenyl group, 2,3,3-trifluoro-2-propenyl group, 1,2,3,3-tetrafluoro-2-propenyl group, and pentafluoro-2-propenyl group.

The fluoroalkynyl group mentioned above is not specifically restricted so long as it is an alkynyl group in which at least one hydrogen atom on a carbon atom is substituted with a fluorine atom. Examples of the fluoroalkynyl group include, for example, a fluoroethynyl group, 3-fluoro-1-propynyl group, 3,3-difluoro-1-propynyl group, 3,3,3-trifluoro-1-propynyl group, 1-fluoro-2-propynyl group, and 1,1-difluoro-2-propynyl group.

The fluoroaryl group mentioned above is not specifically restricted so long as it is an aryl group in which at least one hydrogen atom on a carbon atom is substituted with a fluorine atom. Examples of the fluoroaryl group include, for example, a 2-fluorophenyl group, 3-fluorophenyl group, 4-fluorophenyl group, 2,3-difluorophenyl group, 2,4-difluorophenyl group, 2,5-difluorophenyl group, 2,6-difluorophenyl group, 3,4-difluorophenyl group, 3,5-difluorophenyl group, 2,3,4-trifluorophenyl group, 2,3,5-trifluorophenyl group, 2,3,6-trifluorophenyl group, 2,4,5-trifluorophenyl group, 2,4,6-trifluorophenyl group, 3,4,5-trifluorophenyl group, 2,3,4,5-tetrafluorophenyl group, 2,3,4,6-tetrafluorophenyl group, 2,3,5,6-tetrafluorophenyl group, pentafluorophenyl group, 2-fluoro-1-naphthyl group, 3-fluoro-1-naphthyl group, 4-fluoro-1-naphthyl group, 6-fluoro-1-naphthyl group, 7-fluoro-1-naphthyl group, 8-fluoro-1-naphthyl group, 4,5-difluoro-1-naphthyl group, 5,7-difluoro-1-naphthyl group, 5,8-difluoro-1-naphthyl group, 5,6,7,8-tetrafluoro-1-naphthyl group, heptafluoro-1-naphthyl group, 1-fluoro-2-naphthyl group, 5-fluoro-2-naphthyl group, 6-fluoro-2-naphthyl group, 7-fluoro-2-naphthyl group, 5,7-difluoro-2-naphthyl group, and heptafluoro-2-naphthyl group.

From the standpoint of balance between solubility in organic solvents, charge transporting characteristics, and easy accessibility to raw materials, the fluoroaryl group mentioned above should preferably be a phenyl group which is substituted with at least 3 fluorine atoms, and may be substituted with a cyano group, chlorine atom, bromine atom, iodine atom, nitro group, alkyl group having 1 to 20 carbon atoms, fluoroalkyl group having 1 to 20 carbon atoms or fluoroalkoxy group having 1 to 20 carbon atoms.

The fluoroalkoxy group mentioned above is not specifically restricted so long as it is an alkoxy group in which at least one hydrogen atom on a carbon atom is substituted with a fluorine atom. Examples of the fluoroalkoxy group include, for example, a fluoromethoxy group, difluoromethoxy group, trifluoromethoxy group, 1-fluoroethoxy group, 2-fluoroethoxy group, 1,2-difluoroethoxy group, 1,1-difluoroethoxy group, 2,2-difluoroethoxy group, 1,1,2-trifluoroethoxy group, 1,2,2-trifluoroethoxy group, 2,2,2-trifluoroethoxy group, 1,1,2,2-tetrafluoroethoxy group, 1,2,2,2-tetrafluoroethoxy group, 1,1,2,2,2-pentafluoroethoxy group, 1-fluoropropoxy group, 2-fluoropropoxy group, 3-fluoropropoxy group, 1,1-difluoropropoxy group, 1,2-difluoropropoxy group, 1,3-difluoropropoxy group, 2,2-difluoropropoxy group, 2,3-difluoropropoxy group, 3,3-difluoropropoxy group, 1,1,2-trifluoropropoxy group, 1,1,3-trifluoropropoxy group, 1,2,3-trifluoropropoxy group, 1,3,3-trifluoropropoxy group, 2,2,3-trifluoropropoxy group, 2,3,3-trifluoropropoxy group, 3,3,3-trifluoropropoxy group, 1,1,2,2-tetrafluoropropoxy group, 1,1,2,3-tetrafluoropropoxy group, 1,2,2,3-tetrafluoropropoxy group, 1,3,3,3-tetrafluoropropoxy group, 2,2,3,3-tetrafluoropropoxy group, 2,3,3,3-tetrafluoropropoxy group, 1,1,2,2,3-pentafluoropropoxy group, 1,2,2,3,3-pentafluoropropoxy group, 1,1,3,3,3-pentafluoropropoxy group, 1,2,3,3,3-pentafluoropropoxy group, 2,2,3,3,3-pentafluoropropoxy group, and heptafluoropropoxy group.

The aryl group having 6 to 20 carbon atoms mentioned above (to be referred to as a substituted aryl group for convenience sake), which is substituted with a fluoroalkyl group having 1 to 20 carbon atoms, fluorocycloalkyl group having 3 to 20 carbon atoms, fluorobicycloalkyl group having 4 to 20 carbon atoms, fluoroalkenyl group having 2 to 20 carbon atoms or fluoroalkynyl group having 2 to 20 carbon atoms, and which may be substituted with a cyano group, halogen atom, or fluoroalkoxy group having 1 to 20 carbon atoms, is not specifically restricted so long as it is an aryl group in which at least one hydrogen atom on a carbon atom is substituted with a fluoroalkyl group having 1 to 20 carbon atoms, fluorocycloalkyl group having 3 to 20 carbon atoms, fluorobicycloalkyl group having 4 to 20 carbon atoms, fluoroalkenyl group having 2 to 20 carbon atoms or fluoroalkynyl group having 2 to 20 carbon atoms. Examples of the substituted aryl group include, for example, a 2-(trifluoromethyl)phenyl group, 3-(trifluoromethyl)phenyl group, 4-(trifluoromethyl)phenyl group, 4-ethoxy-3-(trifluoromethyl)phenyl group, 3-fluoro-4-trifluoromethylphenyl group, 4-fluoro-3-trifluoromethylphenyl group, 4-fluoro-2-trifluoromethylphenyl group, 2-fluoro-5-(trifluoromethyl)phenyl group, 3-fluoro-5-(trifluoromethyl)phenyl group, 3,5-di(trifluoromethyl)phenyl group, 2,4,6-tri(trifluoromethyl)phenyl group, 4-(pentafluoroethyl)phenyl group, 4-(3,3,3-trifluoropropyl)phenyl group, 2,3,5,6-tetrafluoro-4-trifluoromethylphenyl group, 4-(perfluorovinyl)phenyl group, 4-(perfluoropropenyl)phenyl group, and 4-(perfluorobutenyl)phenyl group.

From the standpoint of balance between solubility in organic solvents, charge transporting characteristics, and easy accessibility to raw materials, the substituted aryl group mentioned above should preferably be a phenyl group (to be referred to as a substituted phenyl group for convenience sake hereinafter) which is substituted with a fluorocycloalkyl group having 3 to 20 carbon atoms, fluorobicycloalkyl group having 4 to 20 carbon atoms, fluoroalkenyl group having 2 to 20 carbon atoms or fluoroalkynyl group having 2 to 20 carbon atoms, and may be substituted with a cyano group, halogen atom or fluoroalkoxy group having 1 to 20 carbon atoms. A preferable example is a phenyl group having 1 to 3 trifluoromethyl group. A more preferable example is p-trifluoromethylphenyl group.

The fluoroaralkyl group mentioned above is not specifically restricted so long as it is an aralkyl group in which at least one hydrogen atom on a carbon atom is substituted with a fluorine atom. Examples of the fluoroaralkyl group include, for example, a 2-fluorobenzyl group, 3-fluorobenzyl group, 4-fluorobenzyl group, 2,3-difluorobenzyl group, 2,4-difluorobenzyl group, 2,5-difluorobenzyl group, 2,6-difluorobenzyl group, 3,4-difluorobenzyl group, 3,5-difluorobenzyl group, 2,3,4-trifluorobenzyl group, 2,3,5-trifluorobenzyl group, 2,3,6-trifluorobenzyl group, 2,4,5-trifluorobenzyl group, 2,4,6-trifluorobenzyl group, 2,3,4,5-tetrafluorobenzyl group, 2,3,4,6-tetrafluorobenzyl group, 2,3,5,6-tetrafluorobenzyl group, and 2,3,4,5,6-pentafluorobenzyl group.

The aralkyl group having 7 to 20 carbon atoms mentioned above, which is substituted with a fluoroalkyl group having 1 to 20 carbon atoms, fluorocycloalkyl group having 3 to 20 carbon atoms, fluorobicycloalkyl group having 4 to 70 carbon atoms, fluoroalkenyl group having 2 to 20 carbon atoms or fluoroalkynyl group having 2 to 20 carbon atoms, and may be substituted with a cyano group, halogen atom or fluoroalkoxy group having 1 to 20 carbon atoms, is not specifically restricted so long as it is an aralkyl group in which at least one hydrogen atom on a carbon atom is substituted with a fluoroalkyl group having 1 to 20 carbon atoms, fluorocycloalkyl group having 3 to 20 carbon atoms, fluorobicycloalkyl group having 4 to 20 carbon atoms, fluoroalkenyl group having 2 to 20 carbon atoms or fluoroalkynyl group having 2 to 20 carbon atoms. Examples of the aralkyl group include, for example, a 2-trifluoromethylbenzyl group, 3-trifluoromethylbenzyl group, 4-trifluoromethylbenzyl group, 2,4-di(trifluoromethyl)benzyl group, 2,5-di(trifluoromethyl)benzyl group, 2,6-di(trifluoromethyl)benzyl group, 3,5-di(trifluoromethyl)benzyl group, and 2,4,6-ti(trifluoromethyl)benzyl group.

Of these, A is preferably the fluoroalkyl group having 1 to 20 carbon atoms which may be substituted, the fluoroaryl group having 6 to 20 carbon atoms which may be substituted, or the substituted aryl group, more preferably the fluoroaryl group having 6 to 20 carbon atoms which may be substituted, or the substituted aryl group, even more preferably the fluorophenyl group which may be substituted or the substituted phenyl group, and still more preferably the trifluorophenyl group which may be substituted, the tetrafluorophenyl group which may be substituted, the pentafluorophenyl group which may be substituted, and the phenyl group which is substituted with 1 to 3 trifluoromethyl groups.

Listed below are preferable, but unrestricted, examples of A.

[Chemical Formula 5]

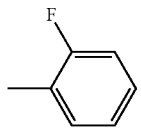
(A1)

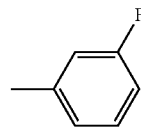
(A2)

(A3)

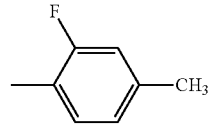
(A4)

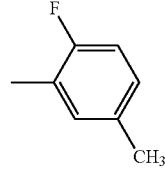
(A5)

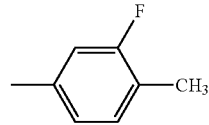
(A6)

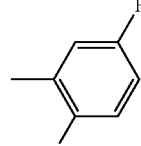
(A7)

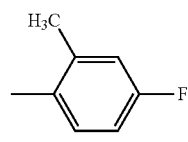
(A8)

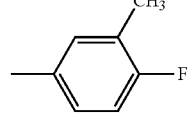
(A9)

[Chemical Formula 6]

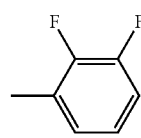
(A10)

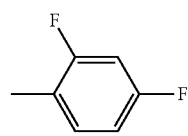
(A11)

-continued
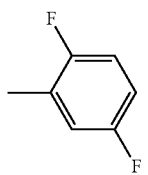 (A12)
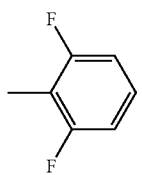 (A13)
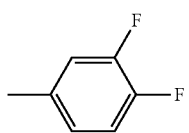 (A14)
 (A15)
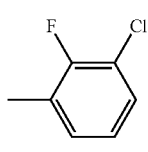 (A16)
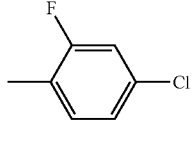 (A17)
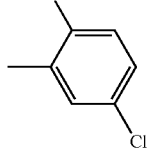 (A18)
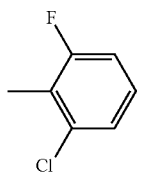 (A19)
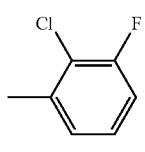 (A20)
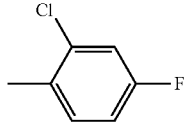 (A21)
-continued
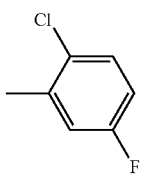 (A22)
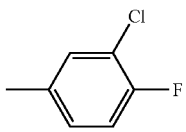 (A23)
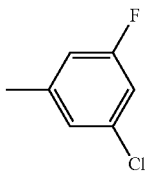 (A24)
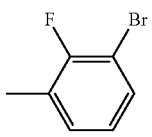 (A25)
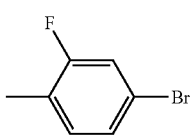 (A26)
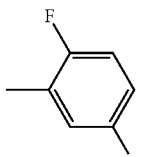 (A27)
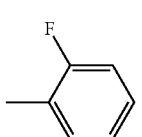 (A28)
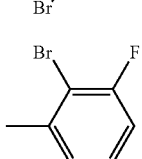 (A29)
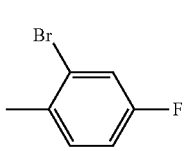 (A30)
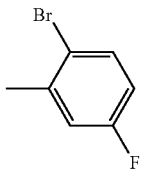 (A31)

-continued
(A32) 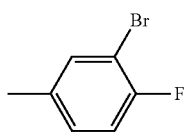
(A33) 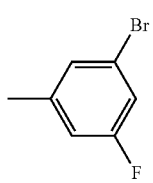
(A34) 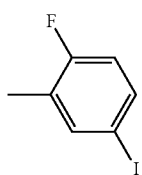
(A35) 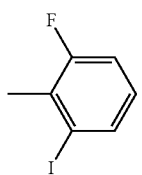
[Chemical Formula 7]
(A36) 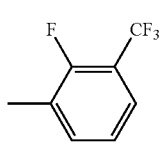
(A37) 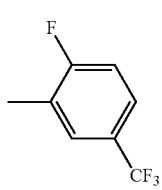
(A38) 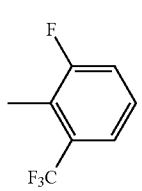
(A39) 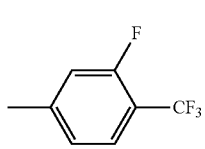
(A40) 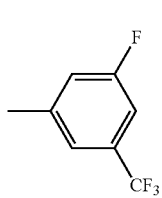
-continued
(A41) 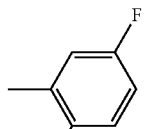
(A42) 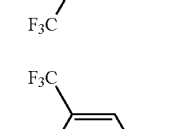
(A43) 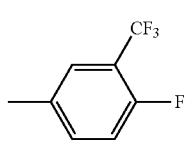
[Chemical Formula 8]
(A44) 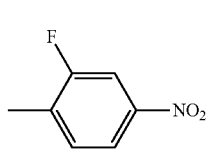
(A45) 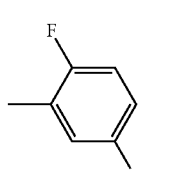
(A46) 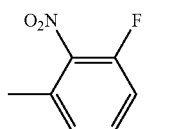
(A47) 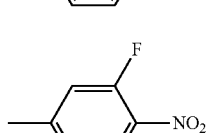
(A48) 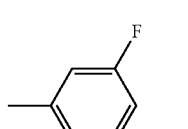
(A49) 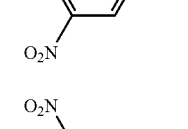
(A50)

-continued
(A51) 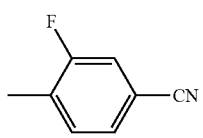
(A52) 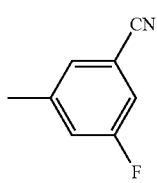
[Chemical Formula 9]
(A53) 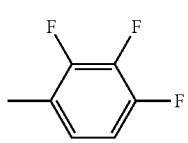
(A54) 
(A55) 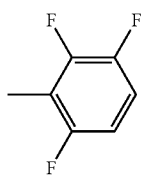
(A56) 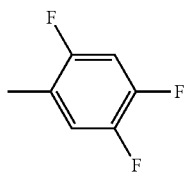
(A57) 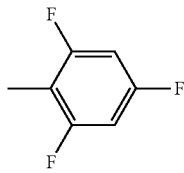
(A58) 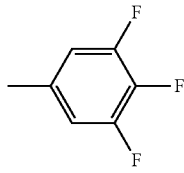
(A59) 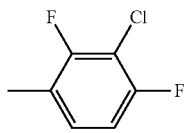
-continued
(A60) 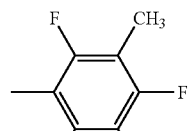
(A61) 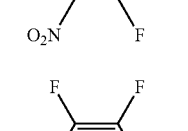
(A62) 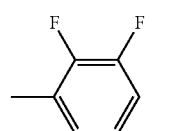
(A63) 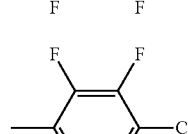
(A64) 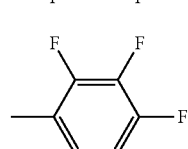
(A65) 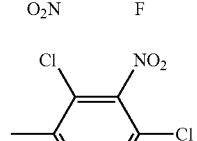
(A66) 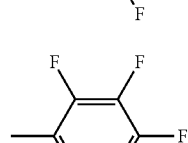
[Chemical Formula 10]
(A67) 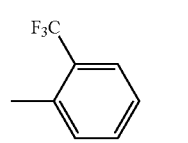
(A68) 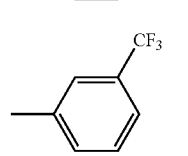

-continued (A69) 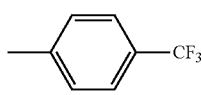

(A70) 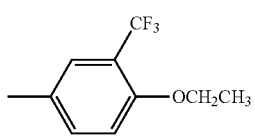

(A71) 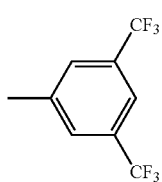

(A72) 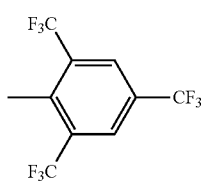

(A73) 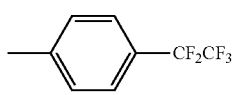

(A74) 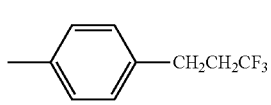

(A75) 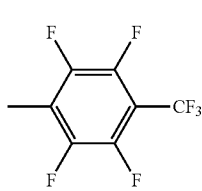

(A76) 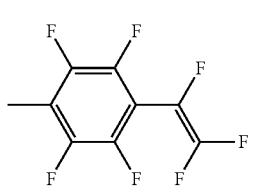

(A77) 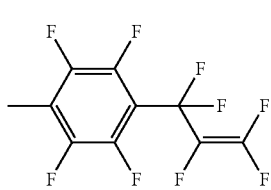

In the formula (1), letter k is an integer of 1 to 20. In order for the oligoaniline derivative to have the solubility of in solvents, the value of k should preferably be up to 10, more preferably up to 8, even more preferably up to 5, and still more preferably up to 4. In order for the oligoaniline derivative to have improved charge-transporting properties, the value of k should be at least 2, and more preferably at least 3. In order for the oligoaniline derivative to have a good balance between solubility and charge-transporting performance, the optimum value of k is 3.

[Method for Synthesis of Fluorine-Containing Oligoaniline Derivative]

The fluorine-containing oligoaniline derivative mentioned above can be synthesized according to the following scheme A which involves the reaction between the amine compound represented by the formula (2A) and the fluorine-containing acid halide represented by the formula (3A). This reaction should preferably be carried out in the presence of a base for better efficiency.

Scheme A

[Chemical Formula 11]

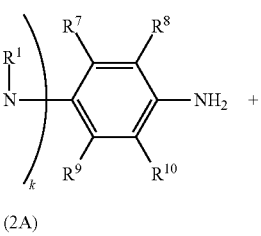

(2A)

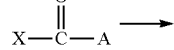

(3A)

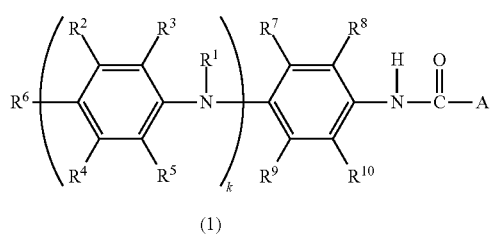

(1)

Herein $R^1$ to $R^{10}$ and letters A and k are as defined above; and X is a halogen atom such as fluorine, chlorine, bromine and iodine, with chlorine or bromine being preferable.

Examples of the amine compound represented by the formula (2A) unrestrictedly include those represented by the following formulas.

[Chemical Formula 12]

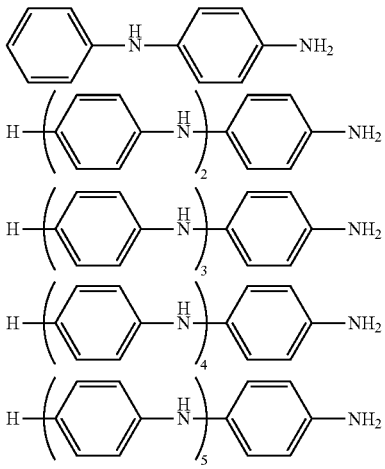

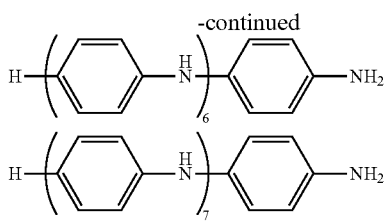

Examples of the fluorine-containing halogen compound represented by the formula (3A) unrestrictedly include 2-fluorobenzoylchloride, 3-fluorobenzoylchloride, 4-fluorobenzoylchloride, 2-fluoro-4-methylbenzoylchloride, 2-fluoro-5-methylbenzoylchloride, 3-fluoro-4-methylbenzoylchloride, 3-fluoro-6-methylbenzoylchloride, 4-fluoro-2-methylbenzoylchloride, 4-fluoro-3-methylbenzoylchloride, 2,3-difluorobenzoylchloride, 2,4-difluorobenzoylchloride, 2,5-difluorobenzoylchloride, 2,6-difluorobenzoylchloride, 3,4-difluorobenzoylchloride, 3,5-difluorobenzoylchloride, 3-chloro-2-fluorobenzoylchloride, 4-chloro-2-fluorobenzoylchloride, 5-chloro-2-fluorobenzoylchloride, 2-chloro-6-fluorobenzoylchloride, 2-chloro-3-fluorobenzoylchloride, 2-chloro-4-fluorobenzoylchloride, 2-chloro-5-fluorobenzoylchloride, 3-chloro-4-fluorobenzoylchloride, 3-chloro-5-fluorobenzoylchloride, 3-bromo-2-fluorobenzoylchloride, 4-bromo-2-fluorobenzoylchloride, 5-bromo-2-fluorobenzoylchloride, 2-bromo-6-fluorobenzoylchloride, 2-bromo-3-fluorobenzoylchloride, 2-bromo-4-fluorobenzoylchloride, 2-bromo-5-fluorobenzoylchloride, 3-bromo-4-fluorobenzoylchloride, 3-bromo-5-fluorobenzoylchloride, 2-fluoro-5-iodobenzoylchloride, 2-fluoro-6-iodobenzoylchloride, 2-fluoro-3-(trifluoromethyl)benzoylchloride, 2-fluoro-5-(trifluoromethyl)benzoylchloride, 2-fluoro-6-(trifluoromethyl)benzoylchloride, 3-fluoro-4-(trifluoromethyl)benzoylchloride, 3-fluoro-5-(trifluoromethyl)benzoylchloride, 3-fluoro-6-(trifluoromethyl)benzoylchloride, 4-fluoro-2-(trifluoromethyl)benzoylchloride, 4-fluoro-3-(trifluoromethyl)benzoylchloride, 2-fluoro-4-nitrobenzoylchloride, 2-fluoro-5-nitrobenzoylchloride, 3-fluoro-2-nitrobenzoylchloride, 3-fluoro-4-nitrobenzoylchloride, 3-fluoro-6-nitrobenzoylchloride, 4-fluoro-2-nitrobenzoylchloride, 4-fluoro-3-nitrobenzoylchloride, 4-cyano-2-fluorobenzoylchloride, 3-cyano-5-fluorobenzoylchloride, 2,3,4-trifluorobenzoylchloride, 2,3,5-trifluorobenzoylchloride, 2,3,6-trifluorobenzoylchloride, 2,4,5-trifluorobenzoylchloride, 2,4,6-trifluorobenzoylchloride, 3,4,5-trifluorobenzoylchloride, 4-chloro-2,4-difluorobenzoylchloride, 2,4-dichloro-5-fluoro-4-nitrobenzoylchloride, 2,4,5-trifluoro-3-methyl-6-nitrobenzoylchloride, 2,3,4,5-tetrafluorobenzoylchloride, 2,3,5,6-tetrafluorobenzoylchloride, 2,3,5,6-tetrafluoro-4-methyl-benzoylchloride, 2,3,4,5-tetrafluoro-6-nitrobenzoylchloride, 2,3,4,5,6-pentafluorobenzoylchloride, 2-(trifluoromethyl)benzoylchloride, 3-(trifluoromethyl)benzoylchloride, 4-(trifluoromethyl)benzoylchloride, 3-trifluoromethyl-4-ethoxybenzoylchloride, 3,5-bis(trifluoromethyl)benzoylchloride, 2,4,6-tris(trifluoromethyl)benzoylchloride, 4-(pentafluoroethyl)benzoylchloride, 4-(3-tetrafluoropropyl)benzoylchloride, 2,3,5,6-tetrafluoro-4-(trifluoromethyl)benzoylchloride, 2,3,5,6-tetrafluoro-4-(trifluorovinyl)benzoylchloride, and 2,3,5,6-tetrafluoro-4-(pentafluoroalkyl)benzoylchloride.

Examples of the base include alkoxides such as t-butoxysodium (t-BuONa) and t-butoxypotassium; fluorides such as lithium fluoride, potassium fluoride, and cesium fluoride; carbonates such as sodium carbonate, potassium carbonate, sodium hydrogen carbonate, and potassium hydrogen carbonate; and amines such as trimethylamine, triethylamine, diisopropylethylamine, tetramethylethylenediamine, pyridine, morpholine, N-methylmorpholine, quinuclidine, 1,4-diazabicyclo[2,2,2]octane, and 4-dimethylaminopyridine. They are not specifically restricted so long as they can be used for the reaction mentioned above. Preferable among them are triethylamine, pyridine, and diisopropylethylamine, which are easy to handle.

The reaction solvent should preferably be an aprotic polar organic solvent, which includes, for example, N,N-dimethylformamide, N,N-dimethylacetamide, N-methylpyrrolidone, 1,3-dimethyl-2-imidazolidinone, dimethylsulfoxide, tetrahydrofuran, and dioxane. Preferable among them are N,N-dimethylformamide, N,N-dimethylacetamide, tetrahydrofuran, and dioxane, which are easy to remove after reaction.

The reaction temperature may range from the melting point to the boiling point of the solvent, depending on the type and amount of the raw material compounds and catalyst. It is usually approximately 0° C. to 200° C., preferably 20° C. to 150° C. The reaction time broadly varies depending on the type and amount of raw material compounds and catalyst and the reaction temperature. It is usually approximately 1 to 24 hours.

The reaction product undergoes ordinary post-treatment to give the fluorine-containing oligoaniline derivative as desired.

Incidentally, the fluorine-containing acid halide represented by the formula (3A) can be obtained by the reaction between a fluorine-containing carboxylic acid (corresponding to it) and an electrophilic halogenating agent (such as thionyl chloride, oxalyl chloride, phosphoryl chloride, sulfuryl chloride, phosphorus trichloride, and phosphorus pentachloride). The fluorine-containing carboxylic acid may be procured from a commercial source or obtained by synthesis according to the known method (disclosed in JP-A H09-67303, JP-A H09-67304, and JP-A 2002-284733).

The fluorine-containing oligoaniline derivative mentioned above can also be synthesized according to the following scheme B or C which involves the reaction (in the presence of a base) between the amine compound represented by the formula (2B) and the fluorine-containing compound represented by the formula (3B) or (3B').

Scheme B

[Chemical Formula 13]

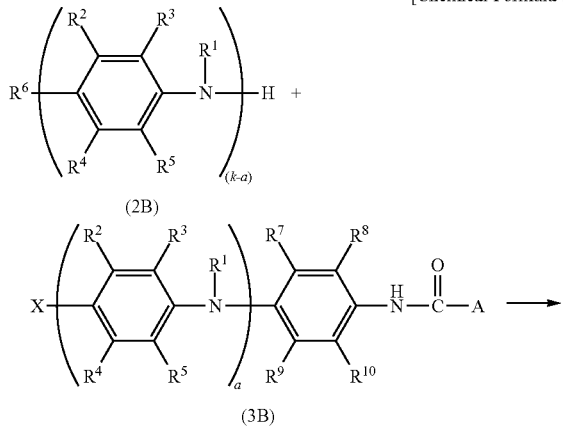

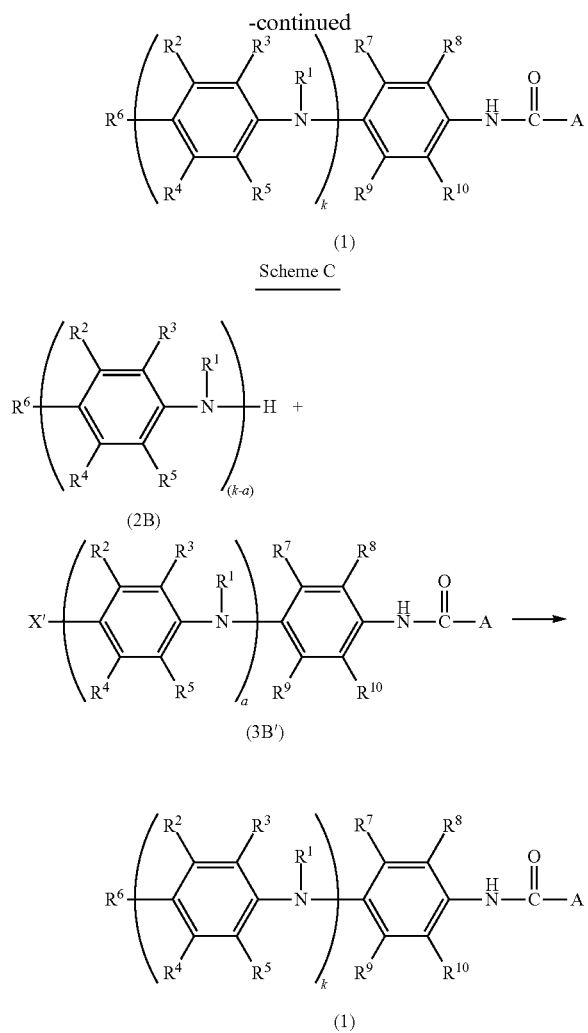

Scheme C

Herein R¹ to R¹⁰ and letters A and k are as defined above; and X is a halogen atom, X' is a pseudo halogen group, and letter a is an integer of 0 to 19, such that k>a.

Examples of the halogen atoms are identical with those mentioned above; preferable ones are bromine atom and iodine atom. Examples of the pseudo halogen group include (fluoro)alkylsulfonyloxy group such as methanesulfonyloxy group, trifluoromethanesulfonyloxy group, and nonafluorobutanesulfonyloxy group; and aromatic sulfonyloxy group such as benzenesulfonyloxy group and toluenesulfonyloxy group.

Examples of the amine compound represented by the formula (2B) include aniline as well as the compounds represented by the formula (2A).

The reactor should be charged with the amine compound represented by the formula (2B) and the fluorine-containing compound represented by the formula (3B) or (3B') such that the ratio of the former to the latter is at least 1 equivalent, preferably from 1:1 to 1:1.2 in terms of equivalent.

Examples of the catalyst used in the reaction mentioned above include, for example, metal catalyst such as copper catalyst such as copper chloride, copper bromide, and copper iodide; and palladium oxide such as tetrakis(triphenylphosphine)palladium (Pd(PPh₃)₄), bis(triphenylphosphine)dichloropalladium (Pd(PPh₃)₂Cl₂), bis(dibenzylidenacetone)palladium (Pd(dba)₂), tris(dibenzylidenacetone)dipalladium (Pd₂(dba)₃), bis(tri-t-butylphosphine)palladium (Pd(P-t-Bu₃)₂), and palladium acetate (Pd(OAc)₂). They may be used alone or in combination with one another.

In order to achieve high yields, it is possible to use the catalyst in combination with any known ligand. Examples of the ligand include tertiary phosphine such as triphenylphosphine, tri-o-tolylphosphine, diphenylmethylphosphine, phenyldimethylphosphine, trimethylphosphine, triethylphosphine, tributylphosphine, tri-t-butylphosphine, di-t-butyl(phenyl)phosphine, di-t-butyl(4-dimethylaminophenyl)phosphine, 1,2-bis(diphenylphosphino)ethane, 1,3-bis(diphenylphosphino)propane, 1,4-bis(diphenylphosphino)butane, and 1,1'-bis(diphenylphosphino)ferrocene; and tertiary phosphite such as trimethyl phosphite, triethyl phosphite, and triphenyl phosphite.

The catalyst should be used in an amount of 0.01 to 0.5 mol, preferably 0.03 to 0.07 mol, per 1 mol of the amine compound represented by the formula (2B). In addition, the ligand should be used in an amount of 0.1 to 5 equivalent, preferably 1 to 4 equivalent, for 1 equivalent of the metal complex.

The general and preferable examples of the base are identical with those mentioned above in relation to the reaction involved in Scheme A.

The solvent for the reaction is not specifically restricted so long as it has no adverse effect on the reaction. Typical examples of the solvent include aliphatic hydrocarbons (such as pentane, n-hexane, n-octane, n-decane, n-decalin), halogenated aliphatic hydrocarbons (such as chloroform, dichloromethane, dichloroethane, and carbon tetrachloride), aromatic hydrocarbons (such as benzene, nitrobenzene, toluene, o-xylene, m-xylene, p-xylene, and mesitylene), halogenated aromatic hydrocarbons (such as chlorobenzene, bromobenzene, o-dichlorobenzene, m-dichlorobenzene, and p-dichlorobenzene), ethers (such as diethyl ether, diisopropyl ether, t-butyl methyl ether, tetrahydrofuran, dioxane, 1,2-dimethoxyethane, and 1,2-diethoxyethane), ketones (such as acetone, methyl ethyl ketone, methyl isobutyl ketone, di-n-butyl ketone, and cyclohexanone), amides (such as N,N-dimethylformamide and N,N-dimethylacetamide), lactams and lactones (N-methylpyrrolidone and γ-butyrolactone), ureas (such as N,N-dimethylimidazolidinone and tetramethyl urea), sulfoxides (dimethylsulfoxide and sulfolane), and nitriles (such as acetonitrile, propionitrile, and butyronitrile). These solvents may be used alone or in combination with one another. Preferable among them are toluene, o-xylene, m-xylene, p-xylene, and dioxane.

The reaction temperature may range from the melting point to the boiling point of the solvent, depending on the type and amount of the raw material compounds and catalyst and the type of the solvent. It is usually approximately 0° C. to 200° C., preferably 20° C. to 150° C. The reaction time broadly varies depending on the type and amount of raw material compounds and catalyst and the reaction temperature. It is usually approximately 1 to 12 hours.

The reaction product undergoes ordinary post-treatment to give the oligoaniline derivative as desired.

The fluorine-containing compound represented by the formula (3B) can be produced according to the scheme D indicated below, in which the compound represented by the formula (4B) is halogenated with a halogenating agent.

Scheme D

[Chemical Formula 14]

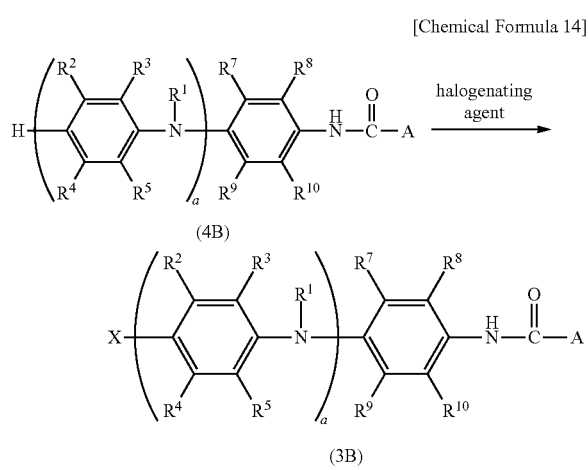

Herein $R^1$ to $R^{10}$ and letters A, X, and a are as defined above.

In addition, the fluorine-containing compound represented by the formula (3B') can be prepared according to the scheme E indicated below, in which the compound represented by the formula (4B') is treated with a pseudo halogenating agent

Scheme E

[Chemcial Formula 15]

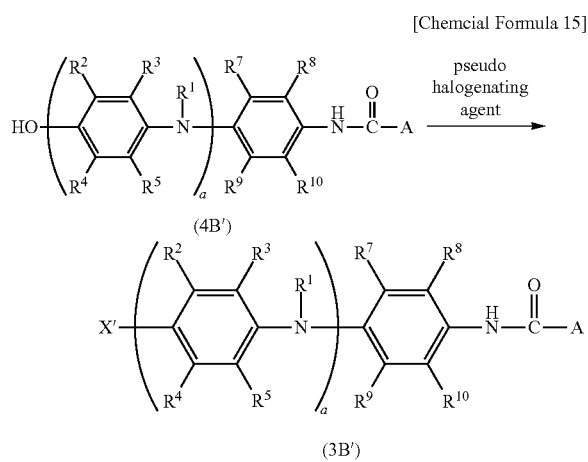

Herein $R^1$ to $R^{10}$ and letters A, X', and a are as defined above.

Examples of the halogenating agent include iodine, N-iodsuccinimide, benzyltrimethylammonium dichloroiodide, 1,3-diiodo-5,5-dimethylhydantoin, hydrogen iodide, bromine, N-bromosuccinimide, benzyltrimethylammonium tribromide, N-bromoacetamide, 2-bromo-2-cyano-N,N-dimethylacetamide, bromodimethylsulfonium bromide, N-bromophthalimide, N-bromosaccharin, 1,3-dibromo-5,5-dimethylhydantoin, dibromoisocyanuric acid, 5,5-dibromomeldrum's acid, 4-dimethylaminopyridiniumbromide perbromide, pyridiniumbromide perbromide, 2,4,4,6-tetrabromo-2,5-cyclohexadienone, tetrabutylammonium tribromide, trimethylphenylammonium tribromide, triphenylphosphin dibromide, chlorine, N-chlorosuccinimide, benzyltrimethylammonium tetrachloroiodide, chloramines B, chloramines T trihydrate, o-chloramine, N-chlorophthalimide, cyanuric chloride, dichloramine T, sodium dichloroisocyanurate, and trichloroisocyanuric acid.

Examples of the pseudo halogenating agent include methanesulfonyl chloride, methanesulfonyl bromide, methanesulfonic acid anhydride, trifluoromethanesulfonyl chloride, trifluoromethanesulfonic acid anhydride, nonafluorobutanesulfonyl chloride, (fluoro)alkylsulfonyl chloride, benzenesulfonyl chloride, and toluenesulfonyl chloride.

The amount of the halogenating agent or pseudo halogenating agent should be 1 to 3 mol, preferably 1.0 to 1.1 mol, per 1 mol of the compound represented by the formula (4B) or (4B').

The solvent for the reaction is not specifically restricted so long as it has no adverse effect on the reaction. Examples of the solvent are the same as those used for production of the fluorine-containing oligoaniline derivative mentioned above. Among preferable examples are N,N-dimethylformamide, N,N-dimethylacetamide, chloroform, and dichloromethane.

The reaction temperature may range from the melting point to the boiling point of the solvent, depending on the type and amount of the raw material compounds and catalyst and the type of the solvent. It is usually approximately 0° C. to 200° C., preferably 0° C. to 50° C. The reaction time broadly varies depending on the type and amount of raw materials and catalyst and the reaction temperature. It is usually approximately 1 to 12 hours.

The reaction product undergoes ordinary post-treatment to give the desired compound.

The compound represented by the formula (4B) can be produced according to the following scheme F which involves the reaction between the amine compound represented by the formula (2A') and the fluorine-containing acid halide represented by the formula (3A), optionally in the presence of the same base as mentioned above.

Scheme F

[Chemical Formula 16]

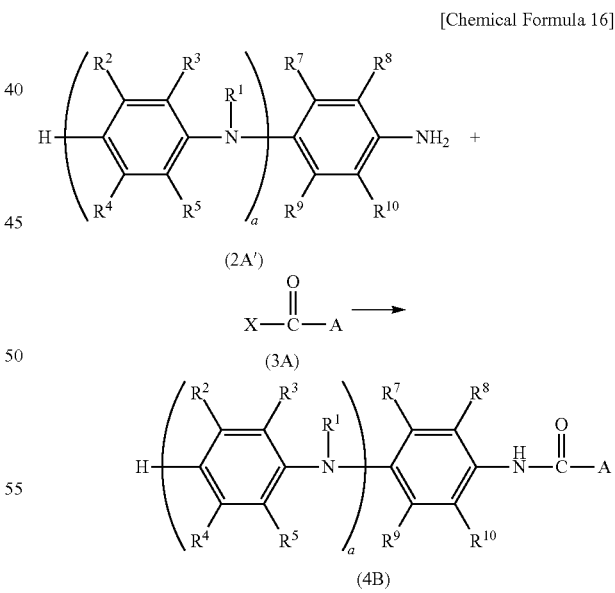

Herein $R^1$ to $R^{10}$ and letters A, X, and a are as defined above.

Examples of the amine compound represented by the formula (2A') include aniline as well as any compound identical with the amine compound represented by the formula (2A). Also, examples of the fluorine-containing acid halide represented by the formula (3A) include the same one as listed above.

The solvent for the reaction is not specifically restricted so long as it has no adverse effect on the reaction. Examples of the solvent include the same one as used for the production of the fluorine-containing oligoaniline derivative mentioned above. Preferable among them are N,N-dimethylformamide, N,N-dimethylacetamide, chloroform, and dichloromethane.

The reaction temperature may range from the melting point to the boiling point of the solvent, depending on the type and amount of the raw material compounds and catalyst and the type of the solvent. It is usually approximately 0° C. to 200° C., preferably 0° C. to 50° C. The reaction time broadly varies depending on the type and amount of raw material compounds and catalyst and the reaction temperature. It is usually approximately 1 to 12 hours.

The reaction product undergoes ordinary post-treatment to give the desired compound.

The amine compound represented by the formula (4B') can be produced according to the following scheme G which involves the reaction between the amine compound represented by the formula (2A") and the fluorine-containing acid halide represented by the formula (3A), optionally in the presence of the same base as mentioned above. The reference of this reaction will be found in J. Med. Chem., 52(4), 1115-1125, (2009).

Scheme G

[Chemical Formula 17]

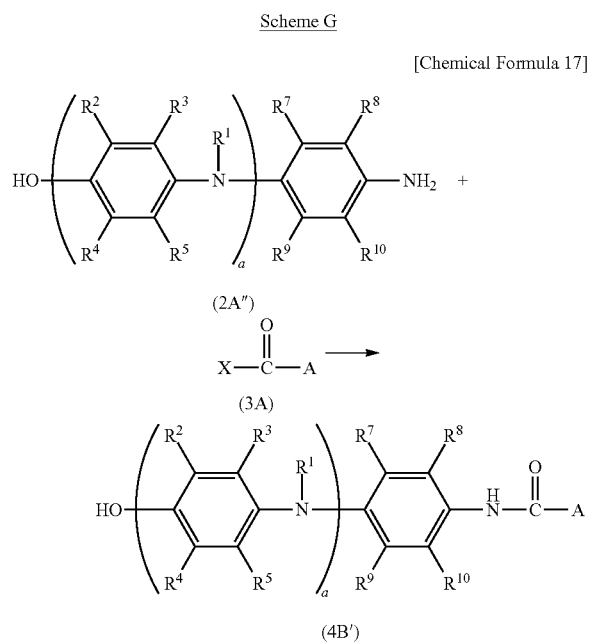

Herein $R^1$ to $R^{10}$ and letters A, X, and a are as defined above.

The solvent for the reaction is not specifically restricted so long as it has no adverse effect on the reaction. Examples of the solvent include the same one as used for the production of the fluorine-containing oligoaniline derivative mentioned above. Preferable among them are N,N-dimethylformamide, N,N-dimethylacetamide, chloroform, and dichloromethane.

The reaction temperature may range from the melting point to the boiling point of the solvent, depending on the type and amount of the raw material compounds and catalyst and the type of the solvent. It is usually approximately 0° C. to 200° C., preferably 0° C. to 50° C. The reaction time broadly varies depending on the type and amount of raw material compounds and catalyst and the reaction temperature. It is usually approximately 1 to 12 hours.

The reaction product undergoes ordinary post-treatment to give the desired compound.

Incidentally, the amine compound represented by the formula (2A") can be synthesized by any known method. For example, the scheme H indicated below gives rise to the compound with a desired chain length.

Scheme H

[Chemical Formula 18]

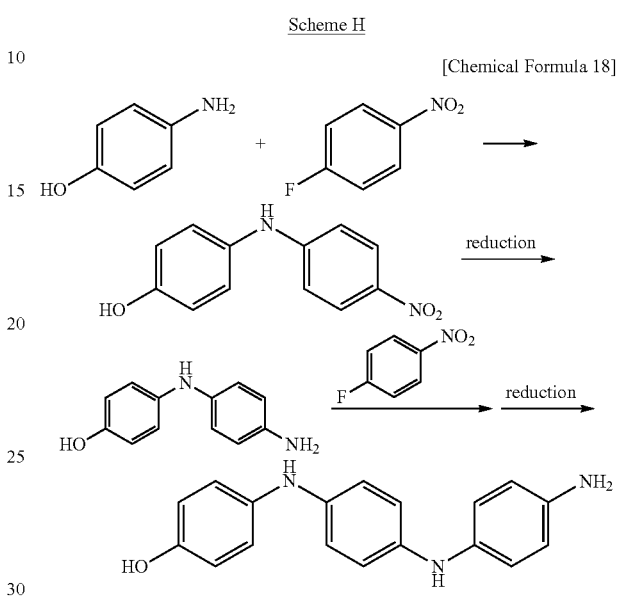

The tables below indicate the unrestricted examples of the oligoaniline derivative represented by the formula (1). The listed compounds are specified by the entries in the rows captioned with "$R^1$ to $R^{10}$," "A," and "k." For example, the compounds identified by (E1) and (E138) are represented by the formulas below.

[Chemical Formula 19]

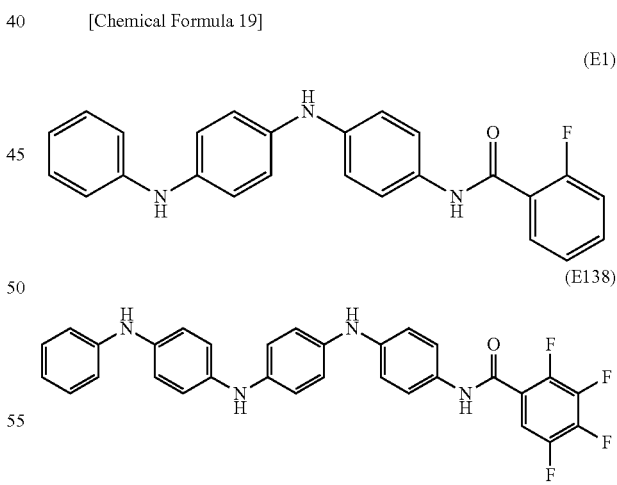

TABLE 1

| Compound | $R^1$~$R^{10}$ | A | k |
|---|---|---|---|
| (E1) | H | (A1) | 2 |
| (E2) | H | (A2) | 2 |
| (E3) | H | (A3) | 2 |
| (E4) | H | (A4) | 2 |

TABLE 1-continued

| Compound | $R^1 \sim R^{10}$ | A | k |
|---|---|---|---|
| (E5) | H | (A5) | 2 |
| (E6) | H | (A6) | 2 |
| (E7) | H | (A7) | 2 |
| (E8) | H | (A8) | 2 |
| (E9) | H | (A9) | 2 |
| (E10) | H | (A10) | 2 |
| (E11) | H | (A11) | 2 |
| (E12) | H | (A12) | 2 |
| (E13) | H | (A13) | 2 |
| (E14) | H | (A14) | 2 |
| (E15) | H | (A15) | 2 |
| (E16) | H | (A16) | 2 |
| (E17) | H | (A17) | 2 |
| (E18) | H | (A18) | 2 |
| (E19) | H | (A19) | 2 |
| (E20) | H | (A20) | 2 |
| (E21) | H | (A21) | 2 |
| (E22) | H | (A22) | 2 |
| (E23) | H | (A23) | 2 |
| (E24) | H | (A24) | 2 |
| (E25) | H | (A25) | 2 |
| (E26) | H | (A26) | 2 |
| (E27) | H | (A27) | 2 |
| (E28) | H | (A28) | 2 |
| (E29) | H | (A29) | 2 |
| (E30) | H | (A30) | 2 |
| (E31) | H | (A31) | 2 |
| (E32) | H | (A32) | 2 |
| (E33) | H | (A33) | 2 |
| (E34) | H | (A34) | 2 |
| (E35) | H | (A35) | 2 |
| (E36) | H | (A36) | 2 |
| (E37) | H | (A37) | 2 |
| (E38) | H | (A38) | 2 |
| (E39) | H | (A39) | 2 |
| (E40) | H | (A40) | 2 |
| (E41) | H | (A41) | 2 |
| (E42) | H | (A42) | 2 |
| (E43) | H | (A43) | 2 |
| (E44) | H | (A44) | 2 |
| (E45) | H | (A45) | 2 |
| (E46) | H | (A46) | 2 |
| (E47) | H | (A47) | 2 |
| (E48) | H | (A48) | 2 |
| (E49) | H | (A49) | 2 |
| (E50) | H | (A50) | 2 |
| (E51) | H | (A51) | 2 |
| (E52) | H | (A52) | 2 |
| (E53) | H | (A53) | 2 |
| (E54) | H | (A54) | 2 |
| (E55) | H | (A55) | 2 |
| (E56) | H | (A56) | 2 |
| (E57) | H | (A57) | 2 |
| (E58) | H | (A58) | 2 |
| (E59) | H | (A59) | 2 |
| (E60) | H | (A60) | 2 |
| (E61) | H | (A61) | 2 |
| (E62) | H | (A62) | 2 |
| (E63) | H | (A63) | 2 |
| (E64) | H | (A64) | 2 |
| (E65) | H | (A65) | 2 |
| (E66) | H | (A66) | 2 |
| (E67) | H | (A67) | 2 |
| (E68) | H | (A68) | 2 |
| (E69) | H | (A69) | 2 |
| (E70) | H | (A70) | 2 |
| (E71) | H | (A71) | 2 |
| (E72) | H | (A72) | 2 |
| (E73) | H | (A73) | 2 |
| (E74) | H | (A74) | 2 |
| (E75) | H | (A75) | 2 |
| (E76) | H | (A76) | 2 |
| (E77) | H | (A77) | 2 |

TABLE 2

| Compound | $R^1 \sim R^{10}$ | A | k |
|---|---|---|---|
| (E78) | H | (A1) | 3 |
| (E79) | H | (A2) | 3 |
| (E80) | H | (A3) | 3 |
| (E81) | H | (A4) | 3 |
| (E82) | H | (A5) | 3 |
| (E83) | H | (A6) | 3 |
| (E84) | H | (A7) | 3 |
| (E85) | H | (A8) | 3 |
| (E86) | H | (A9) | 3 |
| (E87) | H | (A10) | 3 |
| (E88) | H | (A11) | 3 |
| (E89) | H | (A12) | 3 |
| (E90) | H | (A13) | 3 |
| (E91) | H | (A14) | 3 |
| (E92) | H | (A15) | 3 |
| (E93) | H | (A16) | 3 |
| (E94) | H | (A17) | 3 |
| (E95) | H | (A18) | 3 |
| (E96) | H | (A19) | 3 |
| (E97) | H | (A20) | 3 |
| (E98) | H | (A21) | 3 |
| (E99) | H | (A22) | 3 |
| (E100) | H | (A23) | 3 |
| (E101) | H | (A24) | 3 |
| (E102) | H | (A25) | 3 |
| (E103) | H | (A26) | 3 |
| (E104) | H | (A27) | 3 |
| (E105) | H | (A28) | 3 |
| (E106) | H | (A29) | 3 |
| (E107) | H | (A30) | 3 |
| (E108) | H | (A31) | 3 |
| (E109) | H | (A32) | 3 |
| (E110) | H | (A33) | 3 |
| (E111) | H | (A34) | 3 |
| (E112) | H | (A35) | 3 |
| (E113) | H | (A36) | 3 |
| (E114) | H | (A37) | 3 |
| (E115) | H | (A38) | 3 |
| (E116) | H | (A39) | 3 |
| (E117) | H | (A40) | 3 |
| (E118) | H | (A41) | 3 |
| (E119) | H | (A42) | 3 |
| (E120) | H | (A43) | 3 |
| (E121) | H | (A44) | 3 |
| (E122) | H | (A45) | 3 |
| (E123) | H | (A46) | 3 |
| (E124) | H | (A47) | 3 |
| (E125) | H | (A48) | 3 |
| (E126) | H | (A49) | 3 |
| (E127) | H | (A50) | 3 |
| (E128) | H | (A51) | 3 |
| (E129) | H | (A52) | 3 |
| (E130) | H | (A53) | 3 |
| (E131) | H | (A54) | 3 |
| (E132) | H | (A55) | 3 |
| (E133) | H | (A56) | 3 |
| (E134) | H | (A57) | 3 |
| (E135) | H | (A58) | 3 |
| (E136) | H | (A59) | 3 |
| (E137) | H | (A60) | 3 |
| (E138) | H | (A61) | 3 |
| (E139) | H | (A62) | 3 |
| (E140) | H | (A63) | 3 |
| (E141) | H | (A64) | 3 |
| (E142) | H | (A65) | 3 |
| (E143) | H | (A66) | 3 |
| (E144) | H | (A67) | 3 |
| (E145) | H | (A68) | 3 |
| (E146) | H | (A69) | 3 |
| (E147) | H | (A70) | 3 |
| (E148) | H | (A71) | 3 |
| (E149) | H | (A72) | 3 |
| (E150) | H | (A73) | 3 |
| (E151) | H | (A74) | 3 |
| (E152) | H | (A75) | 3 |
| (E153) | H | (A76) | 3 |
| (E154) | H | (A77) | 3 |

TABLE 3

| Compound | $R^1$~$R^{10}$ | A | k |
|---|---|---|---|
| (E155) | H | (A1) | 4 |
| (E156) | H | (A2) | 4 |
| (E157) | H | (A3) | 4 |
| (E158) | H | (A4) | 4 |
| (E159) | H | (A5) | 4 |
| (E160) | H | (A6) | 4 |
| (E161) | H | (A7) | 4 |
| (E162) | H | (A8) | 4 |
| (E163) | H | (A9) | 4 |
| (E164) | H | (A10) | 4 |
| (E165) | H | (A11) | 4 |
| (E166) | H | (A12) | 4 |
| (E167) | H | (A13) | 4 |
| (E168) | H | (A14) | 4 |
| (E169) | H | (A15) | 4 |
| (E170) | H | (A16) | 4 |
| (E171) | H | (A17) | 4 |
| (E172) | H | (A18) | 4 |
| (E173) | H | (A19) | 4 |
| (E174) | H | (A20) | 4 |
| (E175) | H | (A21) | 4 |
| (E176) | H | (A22) | 4 |
| (E177) | H | (A23) | 4 |
| (E178) | H | (A24) | 4 |
| (E179) | H | (A25) | 4 |
| (E180) | H | (A26) | 4 |
| (E181) | H | (A27) | 4 |
| (E182) | H | (A28) | 4 |
| (E183) | H | (A29) | 4 |
| (E184) | H | (A30) | 4 |
| (E185) | H | (A31) | 4 |
| (E186) | H | (A32) | 4 |
| (E187) | H | (A33) | 4 |
| (E188) | H | (A34) | 4 |
| (E189) | H | (A35) | 4 |
| (E190) | H | (A36) | 4 |
| (E191) | H | (A37) | 4 |
| (E192) | H | (A38) | 4 |
| (E193) | H | (A39) | 4 |
| (E194) | H | (A40) | 4 |
| (E195) | H | (A41) | 4 |
| (E196) | H | (A42) | 4 |
| (E197) | H | (A43) | 4 |
| (E198) | H | (A44) | 4 |
| (E199) | H | (A45) | 4 |
| (E200) | H | (A46) | 4 |
| (E201) | H | (A47) | 4 |
| (E202) | H | (A48) | 4 |
| (E203) | H | (A49) | 4 |
| (E204) | H | (A50) | 4 |
| (E205) | H | (A51) | 4 |
| (E206) | H | (A52) | 4 |
| (E207) | H | (A53) | 4 |
| (E208) | H | (A54) | 4 |
| (E209) | H | (A55) | 4 |
| (E210) | H | (A56) | 4 |
| (E211) | H | (A57) | 4 |
| (E212) | H | (A58) | 4 |
| (E213) | H | (A59) | 4 |
| (E214) | H | (A60) | 4 |
| (E215) | H | (A61) | 4 |
| (E216) | H | (A62) | 4 |
| (E217) | H | (A63) | 4 |
| (E218) | H | (A64) | 4 |
| (E219) | H | (A65) | 4 |
| (E220) | H | (A66) | 4 |
| (E221) | H | (A67) | 4 |
| (E222) | H | (A68) | 4 |
| (E223) | H | (A69) | 4 |
| (E224) | H | (A70) | 4 |
| (E225) | H | (A71) | 4 |
| (E226) | H | (A72) | 4 |
| (E227) | H | (A73) | 4 |
| (E228) | H | (A74) | 4 |
| (E229) | H | (A75) | 4 |
| (E230) | H | (A76) | 4 |
| (E231) | H | (A77) | 4 |

[Fluorine-Free Charge-Transporting Substance]

The charge-transporting varnish of the invention contains a fluorine-free charge-transporting substance. Examples of the fluorine-free charge-transporting substance include aniline derivatives, thiophen derivatives, and pyrrol derivatives, which are oligomers capable of transporting charges. The charge-transporting oligomer usually have a molecular weight ranging from 200 to 5,000; however, it should have a molecular weight at least 300, preferably at least 400, and more preferably at least 500, so that it can be made into a varnish that gives rise to a thin film highly capable of transporting charges. In addition, the molecular weight should be up to 4,000, preferably up to 3,000, and more preferably up to 2,000, so that it can be made into a uniform varnish that gives rise to an extremely flat thin film.

Preferable among the above charge-transporting oligomers are aniline derivatives from the standpoint of balance between the solubility in organic solvents and the charge-transporting performance of the resulting thin film. Examples of the aniline derivative include oligoaniline derivative disclosed in JP-A 2002-151272, oligoaniline compound disclosed in WO 2004/105446, oligoaniline compound disclosed in WO 2008/032617, oligoaniline compound disclosed in WO 2008/032616, and aryldiamine compound disclosed in WO 2013/042623.

A preferable example of the aniline derivative is represented by the formula (5) below.

[Chemical Formula 20]

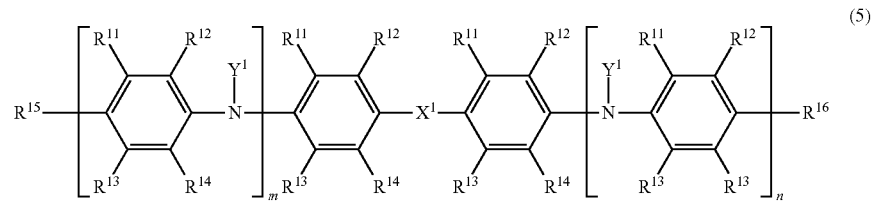

(5)

In the formula (5) above, $X^1$ is $-NY^1-$, $-O-$, $-S-$, $-(CR^{17}R^{18})_L$ or single bond. However, it is $-NY^1-$ when m or n is 0.

$Y^1$ is independently a hydrogen atom, or alkyl group having 1 to 20 carbon atoms, alkenyl group having 2 to 20 carbon atoms or alkynyl group having 2 to 20 carbon atoms which may be substituted with $Z^{11}$, or aryl group having 6 to 20 carbon atoms or heteroaryl group having 2 to 20 carbon atoms which may be substituted with $Z^{12}$.

The alkyl group having 1 to 20 carbon atoms, alkenyl group having 2 to 20 carbon atoms, alkynyl group having 2 to 20 carbon atoms, aryl group having 6 to 20 carbon atoms, and heteroaryl group having 2 to 20 carbon atoms are exemplified by the same ones as mentioned above.

$R^{17}$ and $R^{18}$ are independently a hydrogen atom, chlorine atom, bromine atom, iodine atom, nitro group, cyano group, amino group, aldehyde group, hydroxy group, thiol group, sulfonic acid group, carboxyl group, or alkyl group having 1 to 20 carbon atoms, alkenyl group having 2 to 20 carbon atoms or alkynyl group having 2 to 20 carbon atoms which may be substituted with $Z^{11}$, or aryl group having 6 to 20 carbon atoms or heteroaryl group having 2 to 20 carbon atoms which may be substituted with $Z^{12}$, or $-NHY^2$, $-NY^3Y^4$, $-C(O)Y^5$, $-OY^6$, $-SY^7$, $-SO_3Y^8$, $-C(O)OY^9$, $-OC(O)Y^{10}$, $-C(O)NHY^{11}$ or $-C(O)NY^{12}Y^{13}$.

$Y^2$ to $Y^{13}$ are independently an alkyl group having 1 to 20 carbon atoms, alkenyl group having 2 to 20 carbon atoms or alkynyl group having 2 to 20 carbon atoms which may be substituted with $Z^{11}$, or aryl group having 6 to 20 carbon atoms or heteroaryl group having 2 to 20 carbon atoms which may be substituted with $Z^{12}$.

$Z^{11}$ is a chlorine atom, bromine atom, iodine atom, nitro group, cyano group, amino group, aldehyde group, hydroxy group, thiol group, sulfonic acid group, carboxyl group, or aryl group having 6 to 20 carbon atoms or heteroaryl group having 2 to 20 carbon atoms which may be substituted with $Z^{13}$.

$Z^{12}$ is a chlorine atom, bromine atom, iodine atom, nitro group, cyano group, amino group, aldehyde group, hydroxy group, thiol group, sulfonic acid group, carboxyl group, or alkyl group having 1 to 20 carbon atoms, alkenyl group having 2 to 20 carbon atoms or alkynyl group having 2 to 20 carbon atoms which may be substituted with $Z^{13}$.

$Z^{13}$ is a chlorine atom, bromine atom, iodine atom, nitro group, cyano group, amino group, aldehyde group, hydroxy group group, thiol group, sulfonic acid group, or carboxyl group.

Examples of the alkyl group, alkenyl group, alkynyl group, aryl group and heteroaryl group represented by $R^{17}$, $R^{18}$, and $Y^2$ to $Y^{13}$ include the same one as mentioned above.

Of these, $R^{17}$ and $R^{18}$ should preferably be a hydrogen atom or alkyl group having 1 to 20 carbon atoms which may be substituted with $Z^{11}$, more preferably a hydrogen atom or methyl group which may be substituted with $Z^{11}$, and most desirably a hydrogen atom.

Letter L, which is the number of the divalent groups represented by $-(CR^{17}R^{18})-$, is an integer of 1 to 20, preferably 1 to 10, more preferably 1 to 5, even more preferably 1 to 2, and most preferably 1. In the case where L is at least 2, the members of $R^{17}$ may be identical with or different from one another, and the members of $R^{18}$ may be identical with or different from one another.

A particularly preferable example of $X^1$ is $-NY^1-$ or single bond. $Y^1$ should preferably be a hydrogen atom or alkyl group having 1 to 20 carbon atoms which may be substituted with $Z^{11}$, more preferably a hydrogen atom or methyl group which may be substituted with $Z^{11}$, and most preferably a hydrogen atom.

In the formula (5), $R^{11}$ to $R^{16}$ are independently a hydrogen atom, chlorine atom, bromine atom, iodine atom, nitro group, cyano group, amino group, aldehyde group, hydroxy group, thiol group, sulfonic acid group, carboxyl group, or alkyl group having 1 to 20 carbon atoms, alkenyl group having 2 to 20 carbon atoms or alkynyl group having 2 to 20 carbon atoms which may be substituted with $Z^{11}$, or any one of aryl group having 6 to 20 carbon atoms or heteroaryl group having 2 to 20 carbon atoms which may be substituted with $Z^{12}$, or $-NHY^2$, $-NY^3Y^4$, $-C(O)Y^5$, $-OY^6$, $-SY^7$, $-SO_3Y^8$, $-C(O)OY^9$, $-OC(O)Y^{10}$, $-C(O)NHY^{11}$ or $-C(O)NY^{12}Y^{13}$ (with $Y^2$ to $Y^{13}$ having the same meaning as above). These alkyl group, alkenyl group, alkynyl group, aryl group, and heteroaryl group may be the same one as mentioned above.

In the formula (5), $R^{11}$ to $R^{14}$ each should preferably be a hydrogen atom, halogen atom, alkyl group having 1 to 10 carbon atoms which may be substituted with $Z^{11}$, or aryl group having 6 to 14 carbon atoms which may be substituted with $Z^{12}$, more preferably a hydrogen atom or alkyl group having 1 to 10 carbon atoms, and most preferably a hydrogen atom.

Also, $R^{15}$ and $R^{16}$ each should preferably be a hydrogen atom, chlorine atom, bromine atom, iodine atom, alkyl group having 1 to 10 carbon atoms which may be substituted with $Z^{11}$, aryl group having 6 to 14 carbon atoms which may be substituted with $Z^{12}$, or diphenylamino group which may be substituted with $Z^{12}$ (represented by $-NY^3Y^4$ group wherein $Y^3$ and $Y^4$ are a phenyl group which may be substituted with $Z^{12}$), more preferably a hydrogen atom or diphenylamino group, and most preferably both a hydrogen atom or a diphenylamino group.

A particularly preferable example is one in which $R^{11}$ to $R^{14}$ each is a hydrogen atom or alkyl group having 1 to 10 carbon atoms, $R^{15}$ and $R^{16}$ each is a hydrogen atom or diphenylamino group, and $X^1$ is $-NY^1-$ or single bond, with $Y^1$ being a hydrogen atom or methyl group. A more preferable example is one in which $R^{11}$ to $R^{14}$ each is a hydrogen atom, $R^{15}$ and $R^{16}$ both are a hydrogen atom or diphenylamino group, and $X^1$ is $-NH-$ or a single bond.

In the formula (5), letters of m and n are independently an integer at least 0, with $1 \le m+n \le 20$. From the standpoint of balance between the solubility of the aniline derivative and the charge-transporting performance of its resulting thin film, m and n should have such values as to satisfy $2 \le m+n \le 8$, preferably $2 \le m+n \le 6$, and more preferably $2 \le m+n \le 4$.

In $Y^1$ to $Y^{13}$ and $R^{11}$ to $R^{18}$, $Z^{11}$ is a chlorine atom, bromine atom, iodine atom, or aryl group having 6 to 20 carbon atoms which may be substituted with $Z^{13}$, preferably a chlorine atom, bromine atom, iodine atom, or a phenyl group which may be substituted with $Z^{13}$. The absence of $Z^{11}$ is most desirable.

$Z^{12}$ is preferably a chlorine atom, bromine atom, iodine atom, or alkyl group having 1 to 20 carbon atoms which may be substituted with $Z^{13}$, and more preferably a chlorine atom, bromine atom, iodine atom, or alkyl group having 1 to 4 carbon atoms which may be substituted with $Z^{13}$. The absence of $Z^{12}$ is most desirable.

$Z^{13}$ is preferably a chlorine atom, bromine atom, or iodine atom. The absence of $Z^{13}$ is most desirable.

The substituents in $Y^1$ to $Y^{13}$ and $R^{11}$ to $R^{18}$ should be such that the alkyl group, alkenyl group, and alkynyl group have a carbon number of up to 10, preferably up to 6, and more preferably up to 4. In addition, a carbon number of aryl group and heteroaryl group is up to 14, preferably up to 10, and more preferably up to 6.

The aniline derivative mentioned above can be synthesized by any method without specific restrictions. Typical methods will be found in Bulletin of Chemical Society of Japan, 67, pp. 1749 to 1752 (1994), Synthetic Metals, 84, pp. 119 to 120 (1997), Thin Solid Films, 520(24), pp. 7157 to 7163 (2012), and WO 2008/032617, WO 2008/032616, WO 2008/129947, and WO 2013/084664.

Typical examples of the aniline derivative represented by the formula (5) unrestrictedly include the following. Incidentally, in the formulas below, DPA, Ph, and TPA represent diphenylamino group, phenyl group, and p-(diphenylamino) phenyl group, respectively.

[Chemcial Formula 21]

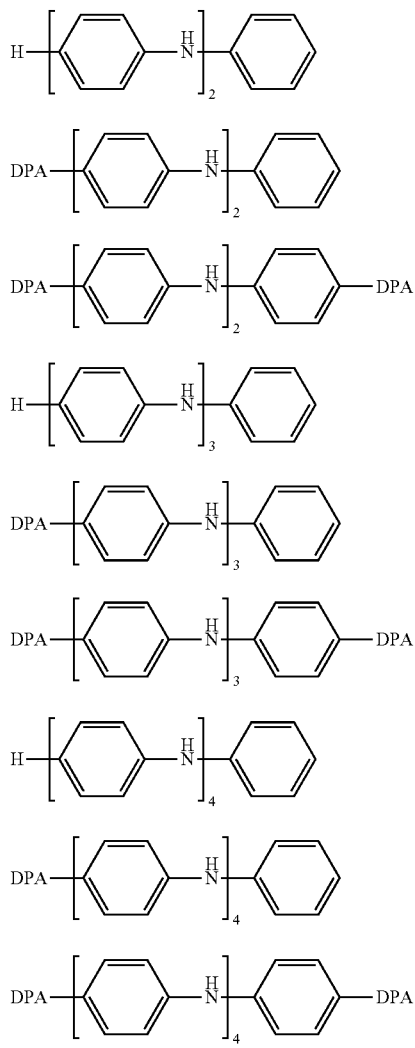

[Chemical Formula 22]

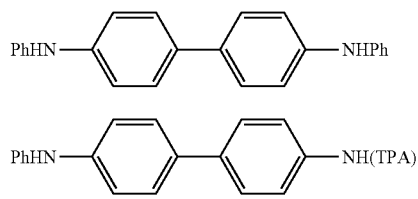

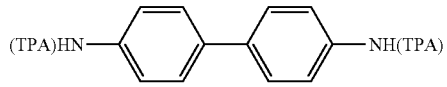

The varnish of the invention should contain the charge-transporting substance in an amount of 0.1 to 20 wt % from the standpoint of preventing precipitation of the charge-transporting substance. The charge-transporting substance of the fluorine-containing oligoaniline derivative and the fluorine-free charge-transporting substance should be used in an amount appropriately determined from the standpoint of the luminance of the resulting organic EL device. The adequate molar ratio of the former to the latter is 1:0.05 to 20, preferably 1:0.5 to 5.

[Organic Solvent]

The charge-transporting varnish of the invention of the invention may be produced using an organic solvent which is highly capable of dissolving the charge-transporting substance and dopant.

Examples of the organic solvent unrestrictedly include cyclohexanone, N,N-dimethylformamide, N,N-dimethylacetamide, N,N-dimethylisobutylamide, N-methylpyrrolidone, and 1,3-dimethyl-2-imidazolidinone. These solvents may be used alone or in combination with one another. The solvent should be used in an amount of 5 to 100 wt % of all the solvents contained in the varnish.

The above solvent should be used such that the charge-transporting substance and dopant are completely dissolved therein or uniformly dispersed therein. Complete dissolution is desirable.

Moreover, the varnish of the invention may additionally contain at least one species of high-viscosity organic solvent which has a viscosity of 10 to 200 mPa·s, preferably 35 to to 150 mPa·s, at 25° C. and a boiling point of 50° C. to 300° C., especially 150° C. to 250° C. at normal (atmospheric) pressure. This additional solvent makes it easy to control the viscosity of the varnish, permits the varnish to constantly give highly flat thin film, and facilitates the production of the vanish suitable for the application method employed.

Examples of the high-viscosity organic solvent unrestrictedly include cyclohexanol, ethyleneglycol, ethyleneglycol diglycidyl ether, 1,3-octyleneglycol, diethyleneglycol, dipropylene glycol, triethylene glycol, tripropylene glycol, 1,3-butanediol, 2,3-butanediol, 1,4-butanediol, propyleneglycol, and hexyleneglycol.

The high-viscosity organic solvent should be preferably used in such an amount that no solids precipitate in the varnish of the invention. A preferable amount is 5 to 90 wt % so long as no solids precipitate.

Another solvent may also be added to improve the wettability on the substrate and adjust the surface tension, polarity, and boiling point of the solvent. The amount of this additional solvent is 1 to 90 wt %, preferably 1 to 50 wt %, of the total amount of the solvents.

Examples of the additional solvents unrestrictedly include propylene glycol monomethyl ether, ethylene glycol monobutyl ether, diethylene glycol diethyl ether, diethylene glycol monomethyl ether, diethylene glycol dimethyl ether, diethylene glycol monoethyl ether acetate, diethylene glycol monobutyl ether acetate, dipropylene glycol monomethyl ether, propylene glycol monomethyl ether acetate, diethylene glycol monoethyl ether, diacetone alcohol, γ-butyrolactone, ethyl lactate, and n-hexyl acetate. They may be used alone or in combination with one another.

The charge-transporting varnish of the invention appropriately varies in viscosity depending on the thickness of the thin film (to be formed from it) and the concentration of solid components therein. An ordinary viscosity is 1 to 50 mPa·s at 25° C. Moreover, the varnish of the invention appropriately varies in the concentration of solid components depending on its viscosity and surface tension and the thickness of the thin film to be formed from it. An ordinary concentration is 0.1 to 10.0 wt %; preferably it is 0.5 to 5.0 wt %, and more preferably it is 1.0 to 3.0 wt %, so that the varnish has improved coating performance. Incidentally, the concentration of solids is defined as the amount of varnish components excluding the organic solvents.

[Dopant]

The charge-transporting varnish of the invention may contain a dopant that improves the ability for the varnish to transport charges depending on the use of the thin film to be produced therefrom. The dopant is not specifically restricted so long as it dissolves in at least one solvent contained in the varnish. Both inorganic dopants and organic dopants may be used. The dopants may be used alone or in combination with one another.

The amount of the dopant in the charge-transporting varnish of the invention should preferably be approximately 0.01 to 20.0 mol, more preferably approximately 0.4 to 5.0 mol, per 1 mol of the fluorine-free charge-transporting varnish.

Examples of the inorganic dopants include inorganic acids such as hydrochloric acid, sulfuric acid, nitric acid, and phosphoric acid; metal halides such as aluminum (iii) chloride ($AlCl_3$), titanium (iv) tetrachloride ($TiCl_4$), boron tribromide ($BBr_3$), boron trifluoride ether complex ($BF_3.OEt_2$), iron (iii) chloride ($FeCl_3$), copper (ii) chloride ($CuCl_2$), antimony (v) pentachloride ($SbCl_5$), antimony (v) pentafluoride ($SbF_5$), arsenic (v) pentafluoride ($AsF_5$), phosphorus pentafluoride ($PF_5$), and tris(4-bromophenyl)aluminum hexachloroantimonate (TBPAH); halides such as $Cl_2$, $Br_2$, $I_2$, ICl, $ICl_3$, IBr, and $IF_4$; and heteropolyacids such as phosphorus-molybdenic acid and phosphotungstic acid. Preferable among these examples are heteropolyacids such as phosphorus-molybdenic acid and phosphotungstic acid.

Examples of the organic dopants include the following aryl sulfone compounds: benzenesulfonic acid, tosyl acid, p-styrenesulfonic acid, 2-naphthalenesulfonic acid, 4-hydroxybenzenesulfonic acid, 5-sulfosalicylic acid, p-dodecylbenzenesulfonic acid, dihexylbenzenesulfonic acid, 2,5-dihexylbenzenesulfonic acid, dibutylnaphthalenesulfonic acid, 6,7-dibutyl-2-naphthalenesulfonic acid, dodecyl naphthalenesulfonic acid, 3-dodecyl-2-naphthalenesulfonic acid, hexylnaphthalenesulfonic acid, 4-hexyl-1-naphthalenesulfonic acid, octylnaphthalenesulfonic acid, 2-octyl-1-naphthalenesulfonic acid, hexylnaphthalenesulfonic acid, 7-hexyl-1-naphthalenesulfonic acid, 6-hexyl-2-naphthalenesulfonic acid, dinonylnaphthalenesulfonic acid, 2,7-dinonyl-4-naphthalenesulfonic acid, dinonylnaphthalenedisulfonic acid, 2,7-dinonyl-4,5-naphthalenedisulfonic acid, 1,4-benzodioxanedisulfonic acid compound disclosed in WO 2005/000832, arylsulfonic acid compound disclosed WO 2006-025342, arylsulfonic acid compound disclosed in WO 2009/096352, and polystyrenesulfonic acid.

Additional preferable dopants are arylsulfonic acid compounds represented by the formula (6) or (7) below.

[Chemical Formula 23]

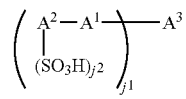

(6)

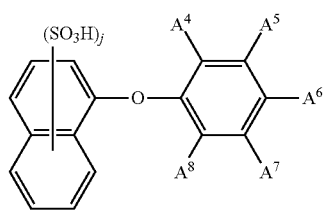

(7)

In the formula (6), $A^1$ is —O— or —S— with —O— being preferable. $A^2$ is a naphthalene ring or anthracene ring with the naphthalene ring being preferable. $A^3$ is a divalent to tetravalent perfluorobiphenyl group. Letter $j^1$ is the number of $A^1$ that bonds with $A^3$, and it is an integer that satisfies $2 \le j^1 \le 4$. $A^3$ should preferably a divalent perfluorobiphenyl group, and letter $j^1$ should preferably be 2. Letter $j^2$ is the number of sulfonic acid groups bonding to $A^2$; it is an integer that satisfies $1 \le j^2 \le 4$, with $j^2$ preferably being 2.

In the formula (7), $A^4$ to $A^8$ are independently a hydrogen atom, halogen atom, cyano group, alkyl group having 1 to 20 carbon atoms, halogenated alkyl group having 1 to 20 carbon atoms, or halogenated alkenyl group having 2 to 20 carbon atoms. At least 3 members of $A^4$ to $A^8$ should be halogen atoms. Letter i is the number of sulfonic acid group bonding to the naphthalene ring; it is an integer that satisfies $1 \le i \le 4$, and it should preferably be 2 to 4, more preferably 2.

Examples of the halogenated alkyl group having 1 to 20 carbon atoms include trifluoromethyl group, 2,2,2-trifluoroethyl group, perfluoroethyl group, 3,3,3-trifluoropropyl group, 2,2,3,3,3-pentafluoropropyl group, perfluoropropyl group, 4,4,4-trifluorobutyl group, 3,3,4,4,4-pentafluorobutyl group, 2,2,3,3,4,4,4-heptafluorobutyl group, and perfluorobutyl group. Examples of the halogenated alkenyl group having 2 to 20 carbon atoms include perfluorovinyl group, 1-perfluoropropenyl group, perfluoroalkyl group, and perfluorobutenyl group.

Examples of the halogen atom and alkyl group having 1 to 20 carbon atoms include the same ones as mentioned above. A preferable example of the halogen atom is a fluorine atom.

Of these, $A^4$ to $A^8$ is preferably a hydrogen atom, halogen atom, cyano group, alkyl group having 1 to 10 carbon atoms, halogenated alkyl group having 1 to 10 carbon atoms, or halogenated alkenyl group having 2 to 10 carbon atoms, with at least 3 members of $A^4$ to $A^8$ being a fluorine atom; more preferably a hydrogen atom, fluorine atom, cyano group, alkyl group having 1 to 5 carbon atoms, halogenated alkyl group having 1 to 5 carbon atoms, and halogenated alkenyl group having 2 to 5 carbon atoms, with at least 3 members of $A^4$ to $A^8$ being a fluorine atom; and even more preferably a hydrogen atom, fluorine atom, cyano group, perfluoroalkyl group having 1 to 5 carbon atoms, and perfluoroalkenyl group having 2 to 5 carbon atoms, with at least 3 members of $A^4$ to $A^8$ being a fluorine atom.

Incidentally, "perfluoroalkyl group" is defined as a group in which all of hydrogen atoms on an alkyl group are substituted with fluorine atoms, and "perfluoroalkenyl group" is defined as a group in which all of hydrogen atoms on an alkenyl group are substituted with fluorine atoms.

Moreover, another preferable example of the dopant is an arylsulfonic acid compound represented by the formula (8) below.

[Chemical Formula 24]

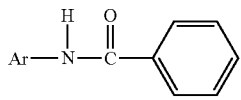
(8)

In the formula (8), Ar is a group represented by the formula (9) or (10).

[Chemical Formula 25]

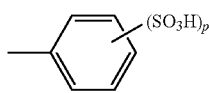
(9)

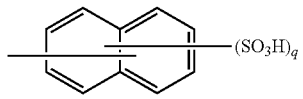
(10)

wherein letter p is an integer of 1 to 5 and letter q is an integer of 1 to 7.

The arylsulonic acid compound represented by the formula (8) can be obtained by the reaction between the amine compound represented by the formula (11) and the acid halide represented by the formula (12), with the resulting salt of arylsulfonic acid subsequently undergoing ion-exchange treatment.

[Chemcial Formula 26]

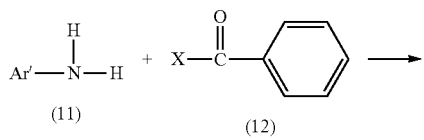

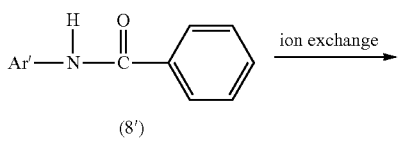

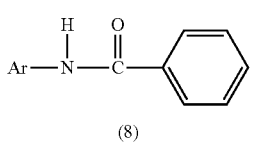
(8)

In the formula, Ar and X are as defined above, and Ar' is the group represented by the formula (9') or (10').

[Chemical Formula 27]

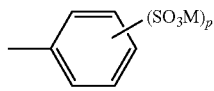
(9')

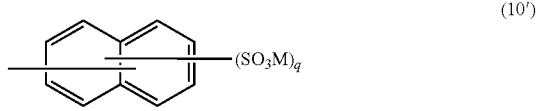
(10')

wherein letters p and q are as defined above, and letter M is an alkali metal atom such as sodium and potassium.

Examples of the amine compound represented by the formula (11) unrestrictedly include the following, for example. Disodium aniline-2,4-disulfonate, disodium aniline-2,5-disulfonate, disodium 8-amino-naphthalene-1,5-disulfonate, disodium 2-amino-naphthalene-1,5-disulfonate, disodium 2-amino-naphthalene-3,6-disulfonate, disodium 7-aminonaphthalene-1,5-disulfonate, disodium 7-aminonaphthalene-2,4-disulfonate, and disodium 7-aminonaphthalene-1,3-disulfonate. Incidentally, the amine compound represented by the formula (11) may be that in the form of hydrate.

Examples of the acid halide represented by the formula (12) include benzoyl chloride, benzoyl bromide, etc.

The reaction should preferably be carried out in an aprotonic polar organic solvent which includes the following, for example. N,N-dimethylformamide, N,N-dimethylacetamide, N-methylpyrrolidone, 1,3-dimethyl-2-imidazolidinone, dimethylsulfoxide, tetrahydrofuran, and dioxane. Preferable among them are N,N-dimethylformamide, N,N-dimethylacetamide, tetrahydrofuran, and dioxane, which can be easily freed of the reaction system.

The reaction temperature usually ranges from −50° C. to the boiling of the solvent involved; it should preferably be 0° C. to 140° C. The reaction time is usually 0.1 to 100 hours.

The reaction is completed by filtration to separate the reaction product and distillation to remove the reaction solvent. In this way there is obtained the arylsulfonate represented by the formula (8'), which is subsequently converted into the arylsulfonic acid compound represented by the formula (8) by treating the sulfonate with a cation exchange resin for protonation.

Incidentally, the acid halide represented by the formula (12) can be obtained by reacting benzoic acid with an electrophilic halogenating agent, such as thionyl chloride, oxalyl chloride, phosphoryl chloride, sulfuryl chloride, phosphorus trichloride, and phosphorus pentachloride.

Preferable examples of the dopant unrestrictedly include phosphomolybdenic acid and phosphotungstic acid and those listed below.

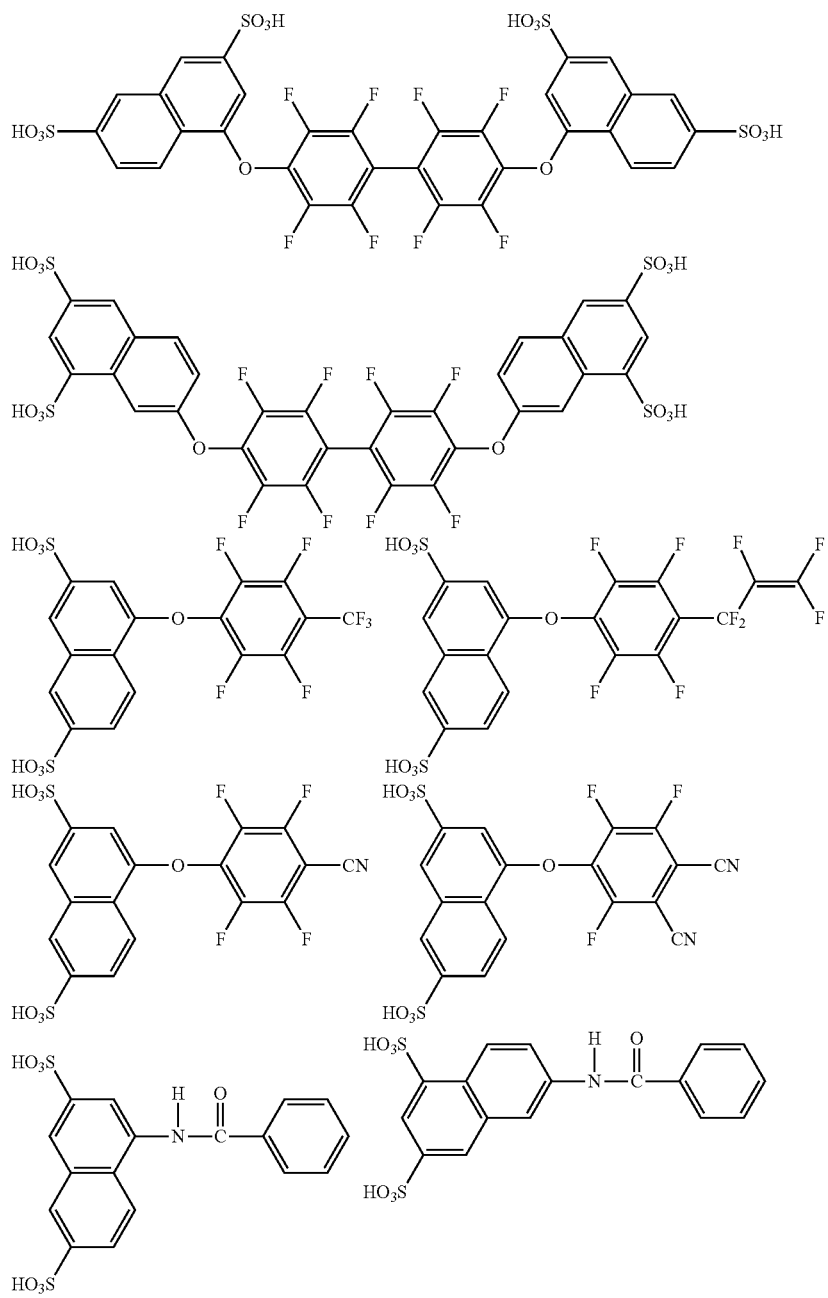

Moreover, the charge-transporting varnish of the invention may be incorporated with any other known charge-transporting substance in an amount not harmful to the effects of the present invention.

The charge-transporting varnish of the invention can be prepared by various methods without specific restrictions. A typical method includes dissolving the oligoaniline derivative of the present invention in a solvent with a high dissolving power and then incorporating the resulting solution with a high-viscosity organic solvent. An alternative method includes dissolving the oligoaniline derivative of the present invention in a mixture of a solvent with a high dissolving power and a high-viscosity organic solvent.

The solution of the charge-transporting substance and dopant which have been dissolved in an organic solvent should preferably be filtered through a filter with an opening of the order of submicron, so that the resulting charge-transporting varnish of the invention invariably gives rise to a highly flat thin film.

[Charge-Transporting Thin Film]

A charge-transporting thin film can be formed on a substrate by coating the charge-transporting varnish of the invention onto the substrate and baking.

Coating with the varnish is accomplished by various methods such as dipping, spin coating, transfer printing, roll coating, brushing, ink jet printing, spraying, slit coating, and others. The application method will require the varnish to be adjusted in viscosity and surface tension.

The charge-transporting varnish of the invention gives rise to a thin film with a uniform flat surface and charge-transporting ability without being affected by the baking condition. Baking is possible in not only the atmospheric air but also inert gas (nitrogen) or vacuum. Baking in the atmospheric air is desirable for reproducible production of thin film with a high charge-transporting ability.

The baking temperature may range from about 100° C. to about 260° C. in view of the intended use of the resulting thin film and the degree of charge-transporting ability to be imparted to the thin film. A preferable baking temperature is about 140° C. to about 250° C., more preferably about 145° C. to about 240° C., in the case where the resulting thin film is used as the hole injection layer of an organic EL device.

The baking time varies depending on the baking temperature and thus cannot be strictly specified, although the baking time generally ranges from about 1 minute to about 1 hour.

In addition, baking may be accomplished at different temperatures at least two stages so as to form the thin film in a more uniform manner or to cause the reaction to take place on the surface of the substrate. Heating may be accomplished by means of a hot plate, oven, etc.

The charge-transporting thin film is not specifically restricted in thickness. A desirable thickness is 5 to 200 nm in the case where it is used as a hole injection layer in an organic EL device. The film thickness may be properly changed by adjusting the concentration of solids in the varnish or by adjusting the amount of the varnish on the substrate at the time of application.

The charge-transporting thin film of the invention appropriately functions as a hole injection layer; however, it may also function as a charge-transporting functional layer such as a hole injection transporting layer.

[Organic EL Device]

The organic EL device of the invention has a pair of electrodes and the above-mentioned charge-transporting thin film between them.

The organic EL device is typically constructed of several components which are arranged as described in (a) to (f) below. The structure described below may optionally be modified such that the light emitting layer and the anode hold between them an electron blocking layer or the light emitting layer and the cathode hold between them a hole blocking layer. Alternatively, the electron blocking layer may have its function served by the hole injection layer, hole transport layer, or the hole injection transport layer; or the hole blocking layer may have its function served by the electron injection layer, electron transport layer, or electron injection transport layer.

(a) anode/hole injection layer/hole transport layer/light emitting layer/electron transport layer/electron injection layer/cathode
(b) anode/hole injection layer/hole transport layer/light emitting layer/electron injection transport layer/cathode
(c) anode/hole injection transport layer/light emitting layer/electron transport layer/electron injection layer/cathode
(d) anode/hole injection transport layer/light emitting layer/electron injection transport layer/cathode
(e) anode/hole injection layer/hole transport layer/light emitting layer/cathode
(f) anode/hole injection transport layer/light emitting layer/cathode "Hole injection layer," "hole transport layer," and "hole injection transport layer" are each defined as a layer which is formed between the anode and the light emitting layer, and it transports holes from the anode to the light emitting layer. In the case where only one layer of hole transporting material is formed between the light emitting layer and the anode, it functions as the "hole injection transport layer." In the case where at least two layers of hole transporting material are formed between the light emitting layer and the anode, the one close to the anode functions as the "hole injection layer" and the other layers function as the "hole transport layer." The hole injection layer and the hole injection transport layer are made from a thin film which is superior in not only ability to accept holes from the anode but also ability to inject holes into the hole transport layer and the light emitting layer.

"Electron injection layer," "electron transport layer," and "electron injection transport layer" are each defined as a layer which is formed between the cathode and the light emitting layer, and it transports electrons from the cathode to the light emitting layer. In the case where only one layer of electron transporting material is formed between the light emitting layer and the cathode, it functions as the "electron injection transport layer." In the case where at least two layers of electron transporting material are formed between the light emitting layer and the cathode, the one close to the cathode functions as the "electron injection layer" and the other layers function as the "electron transport layer."

The "light emitting layer" is an organic layer having a light-emitting function. It is contains a host material and a dopant material in the case where the doping system is employed. The host material stimulates mainly the recombination of electrons and holes and confines excitons in the light emitting layer. The dopant material causes the excitons (resulting from recombination) to emit light efficiently. In the case of phosphorescent device, the host material mainly confines the excitons (generated by the dopant) in the light emitting layer.

The charge-transporting varnish of the invention is used to produce an organic EL device with the help of materials and methods exemplified below, but not restricted to the following.

Prior to the production process, it is desirable to clean the electrode substrate with a liquid such as detergent, alcohol, and pure water. The substrate for the anode should preferably undergo surface treatment such as ultraviolet (UV)-ozone treatment and oxygen-plasma treatment. This surface treatment may be omitted in the case of an anode composed mainly of organic materials.

In the case where the charge-transporting varnish of the invention is made into a thin film which functions as a hole injection layer, an organic EL device of the invention is produced in the following way which is given as an example.

A hole injection layer is formed on an electrode by applying the charge-transporting varnish of the invention on an anode substrate as mentioned above, and baking. On the hole injection layer, a hole transport layer, light emitting layer, electron transport layer, electron injection layer, and cathode are provided in this order. The hole transport layer, light emitting layer, electron transport layer, and electron injection layer may be formed by vapor deposition method or coating method (wet process), depending on the characteristic properties of the materials employed.

Examples of the anode material include a transparent electrode typified by indium-in oxide (ITO) or indium-zinc oxide (IZO), and a metal electrode typified by aluminum or alloy. The planarized one is desirable. It may also be formed from a polythiophene derivative or polyaniline derivative which has a high charge-transporting ability.

Examples of other metals for forming the metal anode include scandium, titanium, vanadium, chromium, manganese, iron, cobalt, nickel, copper, zinc, gallium, yttrium, zirconium, niobium, molybdenum, ruthenium, rhodium, palladium, cadmium, indium, scandium, lanthanum, cerium, praseodymium, neodymium, promethium, samarium, europium, gadolinium, terbium, dysprosium, holmium, erbium, thulium, ytterbium, hafnium, thallium, tungsten, rhenium, osmium, iridium, platinum, gold, titanium, lead, bismuth, and alloys thereof.

Examples of hole transport layer materials include a low molecular weight compound capable of transporting holes, such as triarylamines and oligothiophenes. Examples of the triarylamines include (Triphenylamine)dimer derivative, [(triphenylamine)dimer]spirodimer, N,N'-bis(naphthalen-1-yl)-N,N'-bis(phenyl)-benzidine (α-NPD), N,N'-bis(naphthalen-2-yl)-N,N'-bis(phenyl)-benzidine, N,N'-bis(3-methylphenyl)-N,N'-bis(phenyl)-benzidine, N,N'-bis(3-methylphenyl)-N,N'-bis(phenyl)-9,9-spirobifluorene, N,N'-bis(naphthalen-1-yl)-N,N'-bis(phenyl)-9,9-spirobifluorene, N,N'-bis(3-methylphenyl)-N,N'-bis(phenyl)-9,9-dimethyl-fluorene, N,N'-bis(naphthalen-1-yl)-N,N'-bis(phenyl)-9,9-dimethyl-fluorene, N,N'-bis(3-methylphenyl)-N,N'-bis(phenyl)-9,9-diphenyl-fluorene, N,N'-bis(naphthalen-1-yl)-N,N'-bis(phenyl)-9,9-diphenyl-fluorene, N,N'-bis(naphthalen-1-yl)-N,N'-bis(phenyl)-2,2'-dimethylbenzidine, 2,2',7,7'-tetrakis(N,N-diphenylamino)-9,9-spirobifluorene, 9,9-bis[4-(N,N-bis-phenyl-4-yl-amino)phenyl]-9H-fluorene, 9,9-bis[4-(N,N-bis-naphthalen-2-yl-amino)phenyl]-9H-fluorene, 9,9-bis[4-(N-naphthalen-1-yl-N-phenylamino)-phenyl]-9H-fluorene, 2,2',7,7'-tetrakis[N-naphthalenyl(phenyl)-amino]-9,9-spirobifluorene, N,N'-bis(phenanthren-9-yl)-N,N'-bis(phenyl)-benzidine, 2,2'-bis[N,N-bis(biphenyl-4-yl)amino]-9,9-spirobifluorene, 2,2'-bis(N,N-diphenylamino)-9,9-spirobifluorene, di-[4-(N,N-di(p-tolyl)amino)-phenyl]cyclohexane, 2,2',7,7'-tetra(N,N-di(p-tolyl)amino)-9,9-spirobifluorene, N,N,N',N'-tetra-naphthalen-2-yl-benzidine, N,N,N',N'-tetra-(3-methylphenyl)-3,3'-dimethylbenzidine, N,N'-di(naphthalenyl)-N,N'-di(naphthalen-2-yl)-benzidine, N,N,N',N'-tetra(naphthalenyl)-benzidine, N,N'-di(naphthalen-2-yl)-N,N'-diphenylbenzidine-1,4-diamine, $N^1,N^4$-diphenyl-$N^1,N^4$-di(m-tolyl)benzene-1,4-diamine, $N^2,N^2,N^6,N^6$-tetraphenylnaphthalene-2,6-diamine, tris(4-quinolin-8-yl)phenyl)amine, 2,2'-bis(3-(N,N-di(p-tolyl)amino)phenyl)biphenyl, 4,4',4''-tris[3-methylphenyl(phenyl)amino] triphenylamine (m-MTDATA), and 4,4',4''-tris[1-naphthyl (phenyl)amino]triphenylamine (1-TNATA). An example of the oligothiophene includes 5,5''-bis-{4-[bis(4-methylphenyl)amino]phenyl}-2,2':5',2''-terthiophene (BMA-3T).

The light emitting layer may be formed from one of the following materials: tris(8-quinolinolato)aluminum (iii) (Alq₃), bis(8-quinolinolato)zinc (ii) (Znq₂), bis(2-methyl-8-quinolinolato)-4-(p-phenylphenolato)aluminum (iii) (BAlq), 4,4'-bis(2,2-diphenylvinyl)biphenyl, 9,10-di(naphthalen-2-yl)anthracene, 2-t-butyl-9,10-di(naphthalen-2-yl) anthracene, 2,7-bis[9,9-di(4-methylphenyl)-fluoren-2-yl]-9,9-di(methylphenyl)fluorene, 2-methyl-9,10-bis(naphthalen-2-yl)anthracene, 2-(9,9-spirobifluoren-2-yl)-9,9-spirobifluoorene, 2,7-bis(9,9-spirobifluoren-2-yl)-9,9-spirobifluorene, 2-[9,9-di(4-methylphenyl)-fluoren-2-yl]-9,9-di(4-methylphenyl)fluorene, 2,2'-dipyrenyl-9,9-spirobifluorene, 1,3,5-tris(pyren-1-yl)benzene, 9,9-bis[4-(pyrenyl)phenyl]-9H-fluorene, 2,2'-bi(9,10-diphenylanthracene), 2,7-dipyrenyl-9,9-spirobifluorene, 1,4-di(pyren-1-yl)benzene, 1,3-di(pyren-1-yl)benzene, 6,13-di(biphenyl-4-yl)pentacene, 3,9-di(naphthalen-2-yl) perylene, 3,10-di(naphthalen-2-yl)perylene, tris[4-(pyrenyl)-phenyl]amine, 10,10'-di(biphenyl-4-yl)-9,9'-bianthracene, N,N'-di(naphthalen-1-yl)-N,N'-diphenyl-[1,1':4',1'':4''',1'''-quaterphenyl]4,4'''-diamine, 4,4'di[10-(naphthalen-1-yl)anthracen-9-yl]biphenyl, dibenzo{[f,f']-4,4',7,7'-tetraphenyl}diindeno[1,2,3-cd:1',2'3'-lm]perylene, 1-(7-(9,9'-bianthracen-10-yl)-9,9-dimethyl-9H-fluoren-2-yl)pyrene, 1-(7-(9,9'-bianthracen-10-yl)-9,9-dihexyl-9H-fluoren-2-yl) pyrene, 1,3-bis(carbazol-9-yl)benzene, 1,3,5-tris(carbazol-9-yl)benzene, 4,4',4''-tris(carbazol-9-yl)triphenylamine, 4,4'-bis(carbazol-9-yl)biphenyl (CBP), 4,4'-bis(carbazol-9-yl)-2,2'-dimethylbiphenyl, 2,7-bis(carbazol-9-yl)-9,9-dimethylfluorene, 2,2',7,7'-tetrakis(carbazol-9-yl)-9,9-spirobifluorene, 2,7-bis(carbazol-9-yl)-9,9-di(p-tolyl)fluorene, 9,9-bis[4-(carbazol-9-yl)-phenyl]fluorene, 2,7-bis(carbazol-9-yl)-9,9-spirobifluorene, 1,4-bis(triphenylsilyl)benzene, 1,3-bis(triphenylsilyl)benzene, bis(4-N,N-diethylamino-2-methylphenyl)-4-methylphenylmethane, 2,7-bis(carbazol-9-yl)-9,9-dioctylfluorene, 4,4''-di(triphenylsilyl)-p-terphenyl, 4,4''-di(triphenylsilyl)-biphenyl, 9-(4-t-butylphenyl)-3,6-bis (triphenylsilyl)-9H-carbazole, 9-(4-t-butylphenyl)-3,6-ditrityl-9H-carbazole, 9-(4-t-butylphenyl)-3,6-bis(9-(4-methoxyphenyl)-9H-fluoren-9-yl)-9H-carbazole, 2,6-bis(3-(9H-carbazol-9-yl)phenyl)pyridine, triphenyl(4-(9-phenyl-9H-fluoren-9-yl)phenyl)silane, 9,9-dimethyl-N,N-diphenyl-7-(4-(1-phenyl-1H-benzo[d]imidazol-2-yl)phenyl)-9H-fluorene-2-amine, 3,5-bis(3-(9H-carbazol-9-yl)phenyl) pyridine, 9,9-spirobifluoren-2-yl-diphenyl-phosphineoxide, 9,9'-(5-(triphenylsilyl)-1,3-phenylene)bis(9H-carbazole), 3-(2,7-bis(diphenylphosphoryl)-9-phenyl-9H-fluoroen-9-yl)-9-phenyl-9H-carbazole, 4,4,8,8,12,12-hexa(p-tolyl)-4H-8H-12H-12C-azadibenzo[cd,mn]pyrene, 4,7-di(9H-carbazol-9-yl)-1,10-phenanthroline, 2,2'-bis(4-(carbazol-9-yl) phenyl)biphenyl, 2,8-bis(diphenylphosphoryl)dibenzo[b,d] thiophene, bis(2-methylphenyl)diphenylsilane, bis[3,5-di (9H-carbazol-9-yl)phenyl]diphenylsilane, 3,6-bis(carbazol-9-yl)-9-(2-ethyl-hexyl)-9H-carbazole,
3-(dipenylphosphoryl)-9-(4-diphenylphosphoryl)phenyl)-9H-carbazole, and 3,6-bis[(3,5-diphenyl)phenyl]-9-phenyl-carbazole. The light emitting layer may also be formed by co-deposition from one of the above materials and the light-emitting dopant.

Examples of the light-emitting dopant include 3-(2-benzothiazolyl)-7-(diethylamino)coumarin, 2,3,6,7-tetrahydro-1,1,7,7-tetramethyl-1H,5H,11H-10-(2-benzothiazlyl)quinolizino-[9,9a,1gh]coumarin, quinaeridone, N,N'-dimethyl-quinaeridone, tris(2-phenylpyrldine)iridium(iii) (Ir(ppy)₃), bis(2-phenylpyridine)(acetylacetonate)iridium(iii) (Ir(ppy)₂ (acac)), tris[2-(p-tolyl)pyridine]iridium(iii) (Ir(mppy)₃), 9,10-bis[N,N-di(p-tolyl)amino]anthracene, 9,10-bis[phenyl (m-tolyl)amino]anthracene, bis[2-(2-hydroxyphenyl)benzothiazolato]zinc(ii), $N^{10},N^{10},N^{10},N^{10}$-tetra(p-tolyl)-9,9'-bianthracene-10,10'-diamine, $N^{10},N^{10},N^{10},N^{10}$-tetraphenyl-9,9'-bianthracene-10,10'-diamine, $N^{10},N^{10}$-diphenyl-$N^{10},N^{10}$-dinaphthalenyl-9,9'-bianthracene-10,10'-diamine, 4,4'-bis (9-ethyl-3-carbazovinylene)-1,1'-biphenyl, perylene, 2,5,8, 11-tetra-t-butylperylene, 1,4-bis[2-(3-N-ethylcarbazolyl) vinyl]benzene, 4,4'-bis[4-(di-p-tolylamino)styryl]biphenyl, 4-(di-p-tolylamino)-4'-[(di-p-tolylamino)stylyl]stilbene, bis [3,5-difluoro-2-(2-pyridyl)phenyl-(2-carboxypyridyl)] iridium(iii), 4,4'-bis[4-(diphenylamino)styryl]biphenyl, bis (2,4-difluorophenylpyridinato)tetrakis(1-pyrazolyl)borate-iridium(iii), N,N'-bis(naphthalen-2-yl)-N,N'-bis(phenyl)-tris-(9,9-dimethylfluorenylene), 2,7-bis{2-[phenyl(m-tolyl) amino]-9,9-dimethyl-fluoren-7-yl}-9,9-dimethyl-fluorene, N-(4-((E)-2-(6((E)-4-(diphenylamino)styryl)naphthalen-2-yl)vinyl)-N-phenylbenzenamine, fac-iridium(iii)tris(1-phenyl-3-methylbenzimidazolin-2-yliden-C,C²), mer-iridium (iii)tris(1-phenyl-3-methylbenzimidazolin-2-yliden-C,$C^2$), 2,7-bis[4-(diphenylamino)styryl]-9,9-spirobifluorene, 6-methyl-2-(4-(9-(4-(6-methylbenzo[d]thiazol-2-yl)phenyl) anthracen-10-yl)phenyl)-benzo[d]thiazole, 1,4-di[4-(N,N-diphenyl)amino]styrylbenzene, 1,4-bis(4-(9H-carbazol-9-yl)styryl)benzene, (E)-6-(4-(diphenylamino)styryl)-N,N-diphenylnaphthalene-2-amine, bis(2,4-difluorophenyl-pyridinato)(5-(pyridin-2-yl)-1H-tetrazolate)iridium(iii), bis (3-trifluoromethyl-5-(2-pyridyl)pyrazol)((2,4-difluorobenzyl)diphenylphophinate)-iridium(iii), bis(3-trifluoromethyl-5-(2-pyridyl)pyrazolate)(benzyldiphenylphosphinate) iridium(iii), bis(1-(2,4-difluorobenzyl)-3-methylbenzimidazolium)(3-(trifluoromethyl)-5-(2-pyridyl)-1,2,4-triazolate)iridium(iii), bis(3-trifluoromethyl-5-(2-pyridyl)pyrazolate)(4',6'-difluorophenylpyridinate)iridium(iii), bis(4',6'-difluorophenylpyridinato)(3,5-bis(trifluoromethyl)-2-(2'-pyridyl)pyrolate)-iridium(iii), bis(4',6'-difluorophenylpyridinato)(3-(trifluoromethyl)-5-(2-pyridyl)-1,2,4-triazolate)-iridium(iii), (Z)-6-mesityl-N-(6-mesitylquinolin-2 (1H)-yliden)quinoline-2-amine-$BF_2$, (E)-2-(2-(4-(dimethylamino)styryl)-6-methyl-4H-pyran-4-yliden)malononitrile, 4-(dicyanomethylene)-2-methyl-6-duroridyl-9-enyl-4H-pyrane, 4-(dicyanomethylene)-2-methyl-6-(1,1,7,7-tetramethylduroridyl-9-enyl)-4H-pyrane, 4-(dicyanomethylene)-2-t-butyl-6-(1,1,7,7-tetramethylduroridin-4-yl-vinyl)-4H-pyrane, tris(dibenzoylmethane)phenanthrolineeuropium (iii), 5,6,11,12-tetraphenylnaphthacene, bis(2-benzo[b] thiophen-2-yl-pyridine)(acetylacetonate)iridium(iii), tris(1-phenylisoquinoline)iridium(iii), bis(1-phenylisoquinoline)(acetylacetonate)iridium(iii), bis[1-(9,9-dimethyl-9H-fluoren-2-yl)isoquinoline](acetylacetonate)iridium(iii), bis [2-(9,9-dimethyl-9H-fluoren-2-yl)quinoline](acetylacetonate)iridium(iii), tris[4,4'-di-t-butyl-(2,2')-bipyridine]ruthenium(iii)-bis(hexafluorophosphate), tris(2-phenylquinoline)iridium(iii), bis(2-phenylquinoline)(acetylacetonate) iridium(iii), 2,8-di-t-butyl-5,11-bis(4-t-butylphenyl)-6,12-diphenyltetracene, bis(2-phenylbenzothiozolato)(acetylaceotanate)iridium(iii), 5,10,15,20-tetraphenyltetrabenzoporphyrinplatinum, osmium(ii)bis(3-trifluoromethyl-5-(2-pyridine)pyrazolate)dimethylphenylphosphine, osmium(ii) bis(3-(trifluoromethyl)-5-(4-t-butylpyridyl)-1,2,4-triazolate)-diphenylmethylphosphine, osmium(ii)bis(3-(trifluoromethyl)-5-(2-pyridyl)-1,2,4-triazole)dimethylphenylphosphine, osmium(ii)bis(3-(trifluoromethyl)-5-(4-t-butylpyridyl)-1,2,4-triazolate)-dimethylphenylphosphine, bis [2-(4-n-hexylphenyl)quinoline](acetylacetonate)iridium (iii), tris[2-(4-n-hexylphenyl)quinoline]iridium(iii), tris[2-phenyl-4-methylquinoline]iridium(iii), bis(2-phenylquinoline)(2-(3-methylphenyl)pyridinate)iridium(iii), bis(2-(9,9-diethyl-fluoroen-2-yl)-1-phenyl-1H-benzo[d]imidazolato)(acetylacetonate)-iridium(iii), bis(2-phenylpyridine)(3-(pyridin-2-yl)-2H-chromen-2-onate)iridium(iii), bis(2-phenylquinoline)(2,2,6,6-tetramethylheptane-3,5-dionate) iridium(iii), bis(phenylisoquinoline)(2,2,6,6-tetramethylheptane-3,5-dionate)iridium(iii), iridium(iii)bis (4-phenylthieno[3,2-c]pyridinato-N,$C^2$)acetylacetonate, (E)-2-(2-(t-butyl-6-(2-(2,6,6-trimethyl-2,4,5,6-tetrahydro-1H-pyrolo[3,2,1-ij]quinolin-8-yl)vinyl)-4H-pyran-4-ylidene)malononitrile, bis(3-trifluoromethyl-5-(1-isoquinolyl)pyrazolate)(methyldiphenylphosphine)ruthenium, bis [(4-n-hexylphenyl)isoquinoline](acetylacetonate)iridium (iii), platinum(ii)octaethylporphine, bis(2-methylbenzo[f,h] quinoxaline)(acetylacetonate)iridium(iii), and tris[(4-n-hexylphenyl)xoquinoline]iridium(iii).

The electron transport layer is formed from one of the following materials: 8-hydroxyquinolinolate-lithium, 2,2', 2''-(1,3,5-benzintolyl)-tris(1-phenyl-1-H-benzimidazole), 2-(4-biphenyl)5-(4-t-butylphenyl)-1,3,4-oxadiazole, 2,9-dimethyl-4,7-diphenyl-1,10-phenanthroline, 4,7-diphenyl-1, 10-phenanthroline, bis(2-methyl-8-quinoliolate)-4-(phenylphenolato)aluminum, 1,3-bis[2-(2,2'-bipyridin-6-yl)-1,3,4-oxadiazo-5-yl]benzene, 6,6'-bis[5-(biphenyl-4-yl)-1,3,4-oxadiazo-2-yl]-2,2'-bipyridine, 3-(4-biphenyl)-4-phenyl-5-t-butylphenyl-1,2,4-triazole, 4-(naphthalen-1-yl)-3,5-diphenyl-4H-1,2,4-triazole, 2,9-bis(naphthalen-2-yl)-4,7-diphenyl-1,10-phenanthroline, 2,7-bis[2-(2,2'-bipyridin-6-yl)-1,3,4-oxadiazo-5-yl]-9,9-dimethylfluorene, 1,3-bis[2-(4-t-butylphenyl)-1,3,4-oxadiazo-5-yl]benzene, tris(2,4,6-trimethyl-3-(pyridin-3-yl)phenyl)borane, 1-methyl-2-(4-(naphthalen-2-yl)phenyl)-1H-imidazo[4,5f][1,10] phenanthroline, 2-(naphthalen-2-yl)-4,7-diphenyl-1,10-phenanthroline, phenyl-dipyrenylphosphineoxide, 3,3',5,5'-tetra[(m-pyridyl)-phen-3-yl]biphenyl, 1,3,5-tris[(3-pyridyl)-phen-3-yl]benzene, 4,4'-bis{4,6-diphenyl-1,3,5-triazin-2-yl}biphenyl, 1,3-bis[3,5-di(pyridin-3-yl)phenyl]benzene, bis(10-hydroxybenzo[h]quinolinato)beryllium, diphenylbis (4-(pyridin-3-yl)phenyl)silane, and 3,5-di(pyren-1-yl)pyridine.

The electron injection layer is formed from one of the following compounds: lithium oxide ($Li_2O$), magnesium oxide (MgO), alumina ($Al_2O_3$), lithium fluoride (LiF), sodium fluoride (NaF), magnesium fluoride ($MgF_2$), cesium fluoride (CsF), strontium fluoride ($SrF_2$), molybdenum trioxide ($MoO_3$), aluminum, lithium acetylacetonate (Li(acac)), lithium acetate, and lithium benzoate.

The cathode is formed from one of the following compounds: aluminum, magnesium-silver alloy, aluminum-lithium alloy, lithium, sodium, potassium, and cesium.

In the case where the charge-transporting varnish of the invention gives a thin film which functions as a hole injection layer, the organic EL device of the invention is produced in the following way.

It has been mentioned above that the organic EL device is produced by forming the hole transport layer, light emitting layer, electron transport layer, and electron injection layer by vacuum deposition. The above method may be replaced by sequentially forming the hole transport layer and light emitting layer so as to produce the organic EL device which has the charge transport thin film formed from the charge-transporting varnish of the invention. This method includes steps of applying the charge-transporting varnish of the invention on the anode substrate, thereby forming the hole injection layer by the above method, sequentially forming the hole transport layer and the light emitting layer, and finally forming the cathode by vapor deposition.

The cathode and anode are formed from the same material as mentioned above. The resulting cathode and anode should undergo cleaning and surface treatment in the same way as mentioned above.

The hole transport layer and light emitting layer can be formed by, for example, adding a solvent to a hole transporting polymeric material or light-emitting polymeric material and an optional dopant, dissolving or uniformly dispersing them, applying the resulting solution or uniform dispersion on a hole injection layer or hole transport layer, and then baking the applied layer.

Examples of the hole transport polymeric material include poly[9,9-dihexylfluorenyl-2,7-diyl]-co-(N,N'-bis{p-butylphenyl}-1,4-diaminophenylene)], poly[(9,9-dioctylfluorenyl-2,7-diyl)-co-(N,N'-bis{p-butylphenyl}-1,1'-biphenylene-4,4-diamine)], poly[(9,9-bis{1'-penten-5'- yl}fluorenyl-2,7-diyl)-co-(N,N'-bis{p-butylphenyl}-1,4-diaminophenylene)], poly[N,N'-bis(4-butylphenyl)-N,N'-bis(phenyl)-benzidine]-endocapped with polysilsesquioxane, and poly[(9,9-dioctylfluorenyl-2,7-diyl)-co-(4,4'-(N-(p-butylphenyl))diphenylamine.

Examples of the light-emitting polymeric material include polyfluorene derivative such as poly(9,9-dialkylfluorene) (PDA), polyphenylenevinylene derivative such as poly(2-ethoxy-5-(2'-ethylhexoxy)-1,4-phenylenevinylene) (MEH-PPV), polythiophene derivative such as poly(3-alkylthiophene) (PAT), and polyvinylcarbazole (PVCz).

Examples of the solvent include toluene, xylene, and chloroform. Dissolution or uniform dispersion may be accomplished by stirring, hot stirring, ultrasonic dispersion, or the like.

Examples of the coating method include, but are not limited to, ink jet method, spraying method, dipping method, spin coating method, transfer printing method, roll coating method, and brushing method. Incidentally, coating should preferably be performed in an atmosphere of inert gas such as nitrogen and argon.

Examples of the baking method include methods that involve heating with an oven or hot plate in an inert gas or vacuum.

In the case where the charge-transporting varnish of the invention gives a thin film which functions as a hole injection transport layer, the organic EL device of the invention is produced in the following way.

First, a hole injection transport layer is formed on an node substrate. Then a light emitting layer, electron transport layer, electron injection layer, and cathode are provided in this order on the hole injection transport layer. The light emitting layer, electron transport layer, and electron injection layer are formed in the same way as mentioned above.

The materials for the anode, light emitting layer, light-emitting dopant, electron transport layer, and electron block layer are the same ones as mentioned above.

Incidentally, an optional hole block layer or electron block layer may be formed between the electrode and any arbitrary one of the layers mentioned above. The electron block layer may be formed from tris(phenylpyrazole)iridium, for example.

The anode and cathode, and the layers held between them, are formed from specific materials selected according to the type of the device (for example, bottom emission type or top emission type). Criteria for the selection of adequate materials is given below.

Generally, a device of bottom emission type has a transparent anode on a substrate side so that light emanates from the substrate. By contrast, a device of top emission type has a reflecting anode of metal and a transparent electrode (cathode) opposite to the substrate, so that light emanates from the cathode. Consequently, mention is made of material concerning anode, for example, the device of bottom emission type needs a transparent anode made of ITO or the like, and the device of top emission type needs a reflective anode made of Al/Nd or the like.

The organic EL device of the invention may be sealed together with a desiccant in the usual way according to need so that the device retains its characteristic properties.

EXAMPLES

The present invention will be described in more detail with reference the following Examples, which are not intended to restrict the scope thereof. The apparatuses used in the Examples are listed below.

(1) For observation of $^1$H-NMR: JNM-ECP300 FT NMR SYSTEM, made by JEOL Ltd.
(2) For cleaning of substrate: Substrate cleaning apparatus (vacuum plasma type), made by Choshu Industry Co., Ltd.
(3) For coating of varnish: Spin coater MS-A100, made by Mikasa Co., Ltd.
(4) For measurement of film thickness:
Fine shape measuring apparatus, Surfcorder ET-4000, made by Kosaka Laboratory Ltd.
(5) For production of EL device: Multifunctional vapor deposition system C-E2L1G1-N, made by Choshu Industry Co., Ltd.
(6) For measurement of luminance of EL device:
I-V-L measuring system, made by Tech World Co., Ltd.
(7) For measurement of life of EL device:
System for evaluating the luminance life of the organic EL device, PEL-105S, made by EHC Co., Ltd.

[1] Synthesis of Compounds

[Synthesis Example 1] Synthesis of Oligoaniline Derivative A

[Chemical Formula 29]

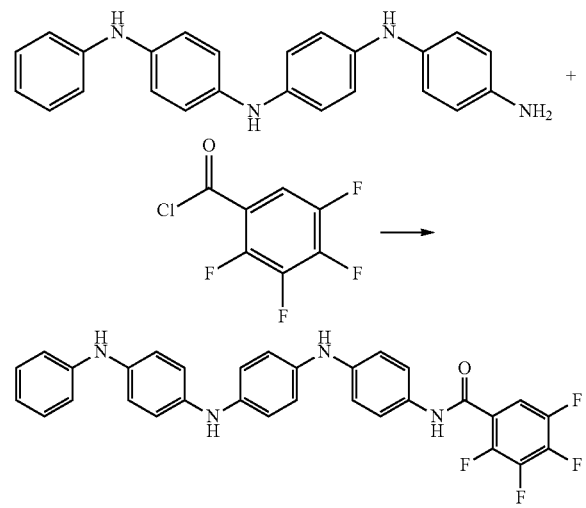

Oligoaniline derivative A

The process for synthesis started with charging a flask with tetraaniline (3.0 g), 2,3,4,5-tetrafluorobonzoyl chloride (1.91 g), and N,N-dimethylacetamide (60 g). With air inside the flask replaced by nitrogen, stirring was continued for 1 hour at room temperature.

After stirring, the flask was charged with 30 mL of aqueous solution of sodium hydroxide (5 mol/L). Stirring was continued further for 30 minutes. The reaction liquid was mixed with ethyl acetate and aqueous solution saturated with sodium chloride, and the mixture was allowed to separate. This step was repeated three times so that the mixture became neutral (pH 7). The organic layer thus obtained was dried with sodium sulfate and then concentrated under reduced pressure. The concentrated solution was given THF (15 mL). The resulting solution was added dropwise to isopropyl alcohol (210 mL). The resulting slurry was stirred for 30 minutes at room temperature.

Finally, the slurry was filtered and the separated solids were dried. Thus there was obtained the desired oligoaniline derivative A. (Yield: 2.94 g). This product gave the $^1$H-NMR data as follows.

¹H-NMR (400 MHz, DMSO-d6) δ [ppm]:

10.35 (s, 1H), 7.83 (s, 1H), 7.79 to 7.68 (m, 3H), 7,49 (d, J=8.0 Hz, 2H), 7.15 (t, J=8.0 Hz, 2H), 7.01 to 6.90 (m, 12H), 6.68 (t, J=8.0 Hz, 1H).

[Synthesis Example 2] Synthesis of Oligoaniline Derivative B

[Chemical Formula 30]

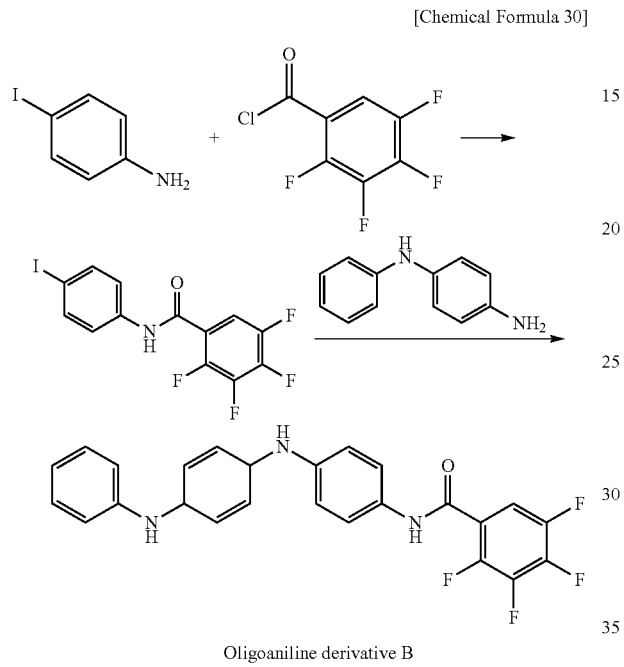

Oligoaniline derivative B

The process for synthesis started with charging a flask with 4-iodoaniline (2.54 g), N,N-dimethylacetamide (25 mL), and triethylamine (1.6 mL). With air inside the flask replaced by nitrogen, the flask was given dropwise 2,3,4,5-tetrafluorobezoylchloride (2.72 g), followed by stirring for 2 hours at room temperature. Then, the reaction liquid was dropped into ion-exchanged water (250 mL), followed by stirring for 1 hour at room temperature. The resulting suspension was filtered off. Thus there was obtained 2,3,4,5-tetrafluoro-N-(4-iodophenyl)benzamide. (Yield: 3.67 g).

Subsequently, a flask was charged with N1-phenylbenzene-1,4-diamine (0.63 g) and 2,3,4,5-tetrafluoro-N-(4-iodophenyl)benzamide (1.51 g), Pd(dba)₂ (80 mg), and t-BuONa (1.67 g). With air inside the flask replaced by nitrogen, the flask was charged with toluene (20 mL) and a separately prepared toluene solution (0.82 mL) containing phenyl-di(t-butyl)phosphine (at a concentration of 75 g/L), followed by stirring for 3.5 hours at 50° C. The reaction solution was cooled to room temperature and filtered. The separated solids were dissolved in 20 mL of N,N-dimethylformamide. The resulting solution was dropped into ion-exchanged water, followed by stirring at room temperature. The resulting suspension was filtered and the separated solids were dried. The dried solids were recrystallized from 1,4-dioxane. Thus there was obtained the oligoaniline derivative B as desired. (Yield: 0.49 g).

[Synthesis Example 3] Synthesis of Oligoaniline Derivative C

[Chemical Formula 31]

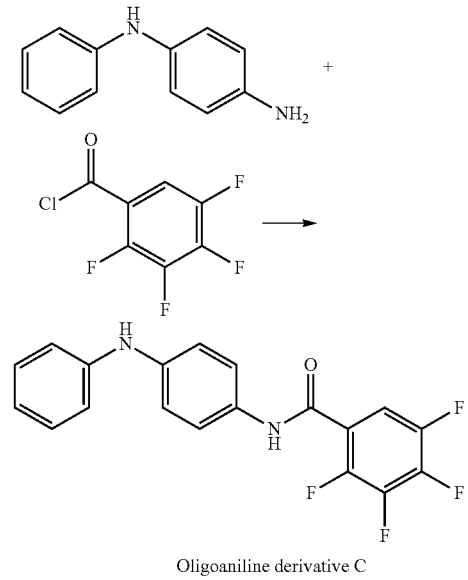

Oligoaniline derivative C

The process for synthesis started with charging a flask with N1-phenylbenzene-1,4-diamine (5.01 g), N,N-dimethylacetamide (25 mL), and triethylamine (4.5 mL). With air inside the flask replaced by nitrogen, the flask was further charged dropwise with 2,3,4,5-tetrafluorobenzoylchloride (6.36 g), followed by stirring for 2 hours at room temperature. After stirring, the reaction liquid was dropped into ion-exchanged water (250 mL), followed by stirring for 1 hour at room temperature. The resulting suspension was filtered, and the separated solids were recrystallized from 1,4-dioxane (10 g) and ethanol (15 g). Thus there was obtained the oligoaniline derivative C as desired. (Yield: 3.36 g). This product gave the ¹H-NMR data as follows.

¹H-NMR (400 MHz, DMSO-d6) δ [ppm]:

10.41 (s, 1H), 8.13 (s, 1H), 7.71 to 7.73 (m, 1H), 7.53 (d, J=7.2 Hz, 2H), 7.18 (t, J=7.6 Hz, 2H), 7.04 (d, J=7.2 Hz, 2H), 7.01 (d, J=7.6 Hz, 2H), 6.74 to 6.78 (m, 1H).

[Synthesis Example 4] Synthesis of Oligoaniline Derivative C'

[Chemical Formula 32]

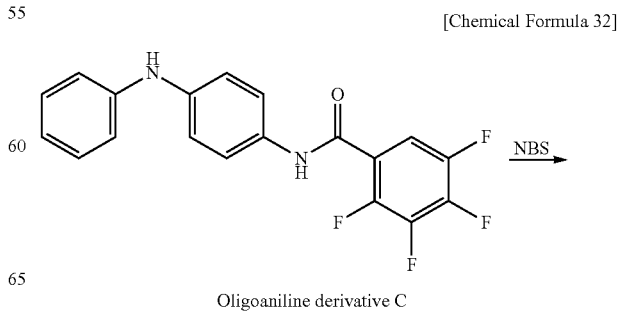

Oligoaniline derivative C

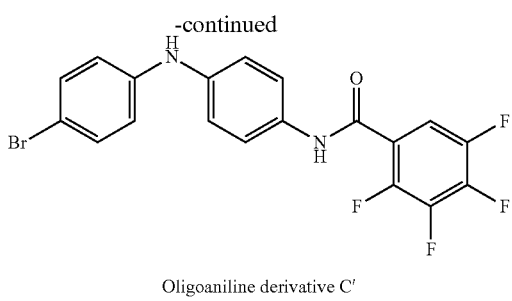

Oligoaniline derivative C'

The process for synthesis started with charging a flask with oligoaniline derivative C (9.85 g), N,N-dimethylformamide (100 mL), and N-bromosuccinimide (5.08 g). With air inside the flask replaced by nitrogen, the reaction liquid was stirred for 3 hours at room temperature. After stirring, the reaction liquid was dropped into ion-exchanged water (1 L), followed by stirring at room temperature. The resulting suspension was filtered, and the separated solids were dried. The resulting product was recrystallized from 1,4-dioxane (10 g) and ethanol (15 g). Thus there was obtained the oligoaniline derivative C' as desired. (Yield: 6.55 g). This product gave the $^1$H-NMR data as follows.

$^1$H-NMR (400 MHz, DMSO-d6) δ [ppm]:
8.16 to 8.19 (m, 1H), 7.83 to 7.86 (m, 1H), 7.53 (d, J=8.8 Hz, 2H), 7.36 (d, J=8.8 Hz), 7.08 (d, J=8.8 Hz, 2H), 6.93 (d, J=8.8 Hz, 2H).

[Synthesis Example 5] Synthesis of Oligoaniline Derivative A

[Chemical Formula 33]

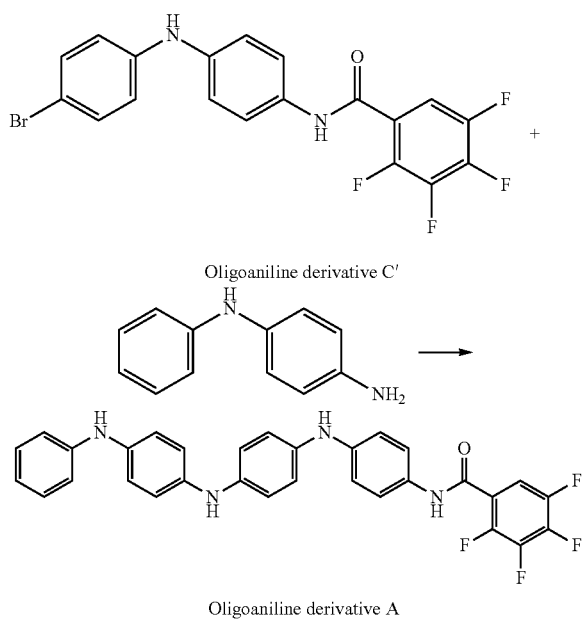

Oligoaniline derivative A

The process for synthesis started with charging a flask with oligoaniline derivative C' (1.31 g), N1-phenylbenzene-1,4-diamine (0.50 g), Pd(dba)$_2$ (63 mg), and t-BuONa (1.34 g). With air inside the flask replaced by nitrogen, the flask was further charged with toluene (15 mL) and a separately prepared toluene solution (0.55 mL) containing phenyl-di(t-butyl)phosphine (at a concentration of 88 g/L), followed by stirring for 5.5 hours at 50° C. The reaction solution was cooled to room temperature and filtered. The separated solids were dissolved in N,N-dimethylformamide. The resulting solution was filtered and the filtrate was dropped into ion-exchanged water, followed by stirring at room temperature. The resulting suspension was filtered and the separated solids were dried. The dried solids were recrystallized from 1,4-dioxane. Thus there was obtained the oligoaniline derivative A as desired. (Yield: 0.72 g). This product was examined by $^1$H-NMR and found to be the same with that obtained in Synthesis Example 1.

[Synthesis Example 6] Synthesis of Aniline Derivative X

[Chemical Formula 34]

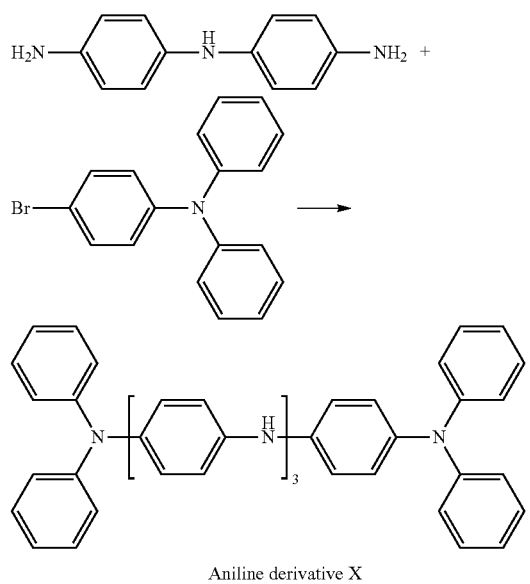

Aniline derivative X

The process for synthesis started with charging a flask with 4,4'-diaminodiphenylamine (3.18 g, 16.0 mmol), 4-bromotriphenylamine (11.4 g, 35.2 mmol), Pd(dba)$_2$ (0.185 g, 0.322 mmol), and t-BuONa (3.38 g, 35.2 mmol). With air inside the flask replaced by nitrogen, the flask was further charged with toluene (200 mL) and PhP(t-Bu)$_2$ (0.142 g, 0.639 mmol), followed by stirring for 5 hours at 80° C. The reaction mixture was cooled to room temperature and given water to suspend reaction. The reaction solution was separated into an aqueous layer and an organic layer. The organic layer was washed with saturated salt solution and dried with MgSO$_4$. The resulting solution was freed of solvent by vacuum distillation. The resulting crude product was purified by silica gel column chromatography (toluene/ethyl acetate). Thus there was obtained the aniline derivative X as desired (Yield: 6.83 g).

[2] Preparation of Charge-Transporting Varnish

[Example 1-1] Preparation of Charge-Transporting Varnish A

Charge-transporting varnish A was prepared by dissolving oligoaniline derivative A (0.051 g) obtained in Synthesis Example 1, phenyltetraaniline (0.169 g) represented by the formula below, and arylsulfonic acid A (0.344 g) represented by the formula below in a mixed solvent of 1,3-dimethyl-2-imidazolidinone (DMI) (6.7 g), cyclohexanol (CHA) (10 g) and propylene glycol (PG) (3.3 g) under nitrogen atmosphere. Incidentally, the phenyltetraaniline was synthesized according to the method disclosed in Bulletin of Chemical Society of Japan, 1994, 67, pp. 1749-1752. The arylsulfonic acid A was synthesized according to the method disclosed in WO 2006/025342.

[Chemical Formula 35]

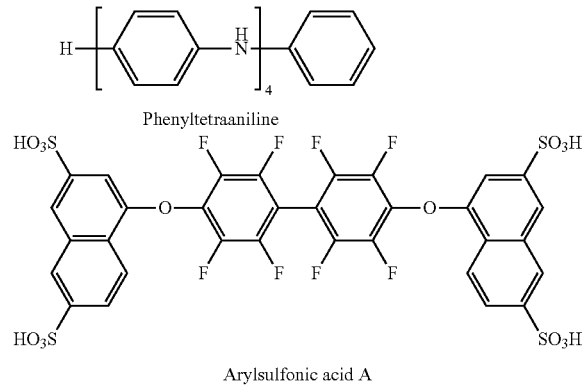

Phenyltetraaniline

Arylsulfonic acid A

[Example 1-2] Preparation of Charge-Transporting Varnish B

Charge-transporting varnish B was prepared by dissolving oligoaniline derivative A (0.083 g) obtained in Synthesis Example 1, aniline derivative X (0.139 g) obtained in Synthesis Example 6, and phosphotungstic acid (0.694 g) (from Kanto Kagaku Co., Inc.) in a mixed solvent of DMI (6.7 g), MIA (10 g) and PG (3.3 g) under nitrogen atmosphere.

[Example 1-3] Preparation of Charge-Transporting Varnish C

Charge-transporting varnish C was prepared by dissolving oligoaniline derivative A (0.051 g) obtained in Synthesis Example 1, aniline derivative X (0.129 g) obtained in Synthesis Example 6, and arylsulfonic acid A (0.383 g) in a mixed solvent of DMI (6.7 g), CHA (10 g) and PG (3.3 g) under nitrogen atmosphere.

[Example 1-4] Preparation of Charge-Transporting Varnish D

Charge-transporting varnish D was prepared by dissolving oligoaniline derivative A (0.073 g) obtained in Synthesis Example 1, N, N'-diphenylbenzidine (0.362 g) (from Tokyo Chemical Industry Co., Ltd.), and arylsulfonic acid A (0.384 g) in a mixed solvent of DMI (14 g), 2,3-butanediole (4 g) and diproplyleneglycol monomethyl ether (2 g) under nitrogen atmosphere.

[Example 1-5] Preparation of Charge-Transporting Varnish E

Charge-transporting varnish E was prepared by dissolving oligoaniline derivative B (0.051 g) obtained in Synthesis Example 2, aniline derivative X (0.129 g) obtained in Synthesis Example 6, and arylsulfonic acid A (0.383 g) in a mixed of DMI (6.7 g), CHA (10 g) and PG (3.3 g) under nitrogen atmosphere.

[Example 1-6] Preparation of Charge-Transporting Varnish F

Charge-transporting varnish F was prepared by dissolving oligoaniline derivative C (0.051 g) obtained in Synthesis Example 3, aniline derivative X (0.129 g) obtained in Synthesis Example 6, and arylsulfonic acid A (0.383 g), which were dissolved in mixed solvents of DMI (6.7 g), CHA (10 g), and PG (3.3 g), under nitrogen atmosphere.

[3] Preparation of Device and Evaluation of Characteristic Properties

In the following Examples and Comparative Examples a glass substrate with dimensions of 25 mm×25 mm×0.7 t in thickness and having a patterned ITO thin film (150 nm thick) is used as the ITO substrate. Prior to use, impurities on the surface ware removed by oxygen plasma cleaning (with 150 W for 30 seconds).

[3-1] Preparation of Single-Layer Device (SLD) and Evaluation of Characteristic Properties Example 2-1

The varnish obtained in Example 1-1 was applied to the ITO substrate by means of a spin coater. This step was followed by pre-baking for 1 minute at 80° C. in the atmospheric air and subsequent baking for 15 minutes at 230° C. Thus there was obtained the ITO substrate coated with a thin film, 40 nm thick.

Further, the coated ITO substrate underwent vacuum deposition with aluminum (at $4.0\times10^{-5}$ Pa). Thus there was obtained a single-layer device coated with a thin aluminum film. The vacuum deposition was carried out at a deposition rate of 0.2 nm/second, so that the aluminum thin film has a thickness of 100 nm.

The resulting single-layer substrate (SLD) was sealed in the following way before evaluation so as to save it from deterioration by oxygen and moisture in the air.

First, the SLD is held between sealing substrates in an atmosphere of nitrogen with an oxygen content up to 2 ppm and a dew point up to −85° C. The SLD and the sealing substrates are joined together with an adhesive (Moresco Moisture Cut WB90US(P), from MORESCO Corporation), which contains a desiccant (HD-071010W-40, from Dynic Corporation). The sealing substrates are irradiated with UV light (with a wavelength of 365 nm and a dosage of 6,000 mJ/cm$^2$), followed by annealing for 1 hour at 80° C. to cure the adhesive.

Examples 2-2 to 2-6

Example 2-1 was repeated to prepare the SLDs except that the varnish obtained in Example 1-1 was replaced by any one of the varnishes obtained in Examples 1-2 to 1-6.

Comparative Example 1

Example 2-1 was repeated to prepare the SLD except that the varnish obtained in Example 1-1 was replaced by an aqueous solution of polyethylenedioxythiophene-polystyrenesulfonic acid (AI4083, from H.C. Starck GmbH) and the baking condition was changed from 15 minutes at 230° C. to 30 minutes at 150° C.

[3-2] Preparation of Hole-Only Device (HOD) and Evaluation of Characteristic Properties Example 3-1

The varnish obtained in Example 1-1 was applied to the ITO substrate by means of a spin coater. This step was followed by pre-baking for 1 minute at 80° C. in the atmospheric air and subsequent baking for 15 minutes at 230° C. Thus there was obtained the ITO substrate coated with a thin film (hole injection layer), 40 nm thick.

Further, the coated ITO substrate underwent vacuum deposition with α-NPD and aluminum (at $2.0 \times 10^{-5}$ Pa). Thus there was obtained the desired hole-only device. The vacuum deposition was carried out at a deposition rate of 0.2 nm/second, so that the thin film of α-NPD and aluminum has a thickness of 20 nm and 100 nm, respectively.

The resulting HOD was sealed with sealing substrates in the same way as mentioned above before evaluation so as to save it from deterioration by oxygen and moisture in the air.

Examples 3-2 to 3-6

Example 3-1 was repeated to prepare the HODs in the same way as in Example 3-1 except that the varnish obtained in Example 1-1 was replaced by the one obtained in any one of Examples 1-2 to 1-6.

Comparative Example 2

Example 3-1 was repeated to prepare the HOD except that the varnish obtained in Example 1-1 was replaced by an aqueous solution of polyethylenedioxythiophene-polystyrenesulfonic acid (AI4083, from H.C. Starck GmbH) and the baking condition was changed from 15 minutes at 230° C. to 30 minutes at 150° C.

The samples of the SLDs and HODs prepared in the above Examples and Comparative Examples were examined for current density at a drive voltage of 3 V. The results are indicated in Table 4. Table 4 also indicates the relative intensity of the current density of HOD to the current density of SLD. This relative intensity suggests that holes are being efficiently supplied to the hole transport layer in proportion to its value.

TABLE 4

| | Charge-transporting varnish | Current density (mA/cm$^2$) | | HOD/SLD (%) |
|---|---|---|---|---|
| | | SLD | HOD | |
| Examples 2-1, 3-1 | A | 3,160 | 1,050 | 33.1 |
| Examples 2-2, 3-2 | B | 4,810 | 1,340 | 27.8 |
| Examples 2-3, 3-3 | C | 2,800 | 1,130 | 40.5 |
| Examples 2-4, 3-4 | D | 1,410 | 222 | 15.8 |
| Examples 2-5, 3-5 | E | 3,010 | 808 | 26.8 |
| Examples 2-6, 3-6 | F | 2,990 | 1,140 | 38.1 |
| Comparative Examples 1, 2 | PEDOT:PSS aq. solution | 3,210 | 328 | 10.2 |

It is noted from Table 4 that all the devices having the hole injection layer formed from the charge-transporting varnish of the invention give a high value of relative intensity for the current density of HOD to the current density of SLD.

[3-3] Preparation of Organic EL Device and Evaluation of Characteristic Properties—1

Example 4-1

The varnish obtained in Example 1-1 was applied to the ITO substrate with the help of a spin coater, followed by drying for 1 minute at 80° C. and baking for 15 minutes at 230° C. in the air. Thus there was obtained an ITO substrate coated with a uniform thin film (hole injection layer), 40 nm thick.

The hole injection layer was coated with a layer of α-NPD (20 nm thick) by vacuum deposition (at $2.0 \times 10^{-5}$ Pa). The rate of deposition was 0.2 nm/second. The top surface was coated with a thin film (40 nm thick) by co-deposition with CBP and Ir(ppy)$_3$. The rate of co-deposition was adjusted so that Ir(ppy)$_3$ accounts for 6%. The top surface was further coated sequentially with a thin film of BAlq, lithium fluoride, and aluminum. Thus there was obtained an organic EL device. The rate of deposition was 0.2 nm/second for BAlq and aluminum and 0.02 nm/second for lithium fluoride. The thin film of BAlq, lithium fluoride, and aluminum has a thickness of 20 nm, 0.5 nm, and 100 nm, respectively.

The resulting organic EL device was sealed with sealing substrates in the same way as mentioned above before evaluation so as to save it from deterioration by oxygen and moisture in the air. The characteristic properties were evaluated in the same way as mentioned above.

Examples 4-2 to 4-4

The same procedure as in Example 4-1 was repeated to prepare the organic EL devices except that the varnish obtained in Example 1-1 was replaced by the one obtained in Examples 1-2 to 1-4.

Comparative Example 3

The same procedure as in Example 4-1 was repeated to prepare the organic EL device except that the varnish obtained in Example 1-1 was replaced by an aqueous solution of polyethylenedioxythiophene-polystyrenesulfonic acid (AI4083, from H.C. Starck GmbH) and the baking condition was changed from 15 minutes at 230° C. to 30 minutes at 150° C.

The samples of the organic EL devices mentioned above were examined for voltage, current density, current efficiency, and half life, with the luminance set at 5,000 cd/m$^2$. (The half life was measured with the initial luminance set at 5,000 cd/m$^2$.) The results are indicated in Table 5. Incidentally, each sample has the light emitting surface measuring 2 mm by 2 mm.

TABLE 5

| | Charge-transporting varnish | Voltage (V) | Current density (mA/cm$^2$) | Current efficiency (cd/A) | Half life (h) |
|---|---|---|---|---|---|
| Example 4-1 | A | 9.62 | 18.86 | 26.53 | 159 |
| Example 4-2 | B | 9.62 | 21.71 | 23.01 | 170 |
| Example 4-3 | C | 9.77 | 18.22 | 27.46 | 132 |
| Example 4-4 | D | 9.69 | 17.90 | 27.94 | 156 |
| Comparative Example 3 | PEDOT:PSS aq. solution | 9.84 | 18.12 | 27.60 | 26.5 |

It is noted from Table 5 that the charge-transporting varnish of the invention gives rise to the organic EL devices which has a low driving voltage and a long half life.

[3-4] Preparation of Organic EL Devices and Evaluation of Characteristic Properties—2

Example 5-1

The varnish obtained in Example 1-3 was applied to the ITO substrate with the help of a spin coater, followed by drying for 1 minute at 80° C. and baking for 15 minutes at 230° C. in the air. Thus there was obtained an ITO substrate coated with a uniform thin film (hole injection layer), 40 nm thick.

The hole injection layer was coated by spin coating with a 0.7 wt % xylene solution of poly[(9,9-dioctylfluorenyl-2, 7-diyl)-co-(4,4'-(N-(p-butylphenyl))diphenylamine)] (from Wako Pure Chemical Industries, Ltd.), followed by baking for 10 minutes at 150° C. Thus, the hole injection layer was coated with a uniform thin film (20 nm thick) on the hole transport layer.

The top surface was further coated with a thin laminated film (40 nm thick) by vapor co-deposition with CBP and Ir(ppy)$_3$ in a vacuum at $2.0 \times 10^{-5}$ Pa. The rate of co-deposition was adjusted so that Ir(ppy)$_3$ accounts for 6%. The top surface was further coated sequentially with a thin film of BAlq, lithium fluoride, and aluminum. Thus there was obtained an organic EL device. The rate of deposition was 0.2 nm/second for BAlq and aluminum and 0.02 nm/second for lithium fluoride. The thin film of BAlq, lithium fluoride, and aluminum has a thickness of 20 nm, 0.5 nm, and 100 nm, respectively.

The resulting organic EL device was sealed with sealing substrates in the same way as mentioned above before evaluation so as to save it from deterioration by oxygen and moisture in the air. The characteristic properties were evaluated in the same way as mentioned above.

Examples 5-2 and 5-3

Example 5-1 was repeated to prepare the organic EL devices in the same way as in Example 5-1 except that the varnish obtained in Example 1-3 was replaced by the one obtained in Examples 1-5 and 1-6.

The samples of the organic EL devices mentioned above were examined for voltage, current density, current efficiency, and half life, with the luminance set at 1,000 cd/m$^2$. (The half life was measured with the initial luminance set at 1,000 cd/m$^2$.) The results are indicated in Table 6. Incidentally, each sample has the light emitting surface measuring 2 mm by 2 mm.

TABLE 6

| | Charge-transporting varnish | Voltage (V) | Current density (mA/cm$^2$) | Current efficiency (cd/A) | Half life (h) |
| --- | --- | --- | --- | --- | --- |
| Example 5-1 | C | 7.95 | 3.76 | 26.57 | 130 |
| Example 5-2 | E | 7.19 | 3.69 | 27.10 | 158 |
| Example 5-3 | F | 7.67 | 3.64 | 27.42 | 133 |

It is noted from Table 6 that the charge-transporting varnish of the invention gives rise to the organic EL devices which has a low driving voltage and a long half life.

The invention claimed is:

1. A charge-transporting varnish comprising a charge-transporting substance of a fluorine-containing oligoaniline derivative represented by the formula (1) below, a fluorine-free charge-transporting substance, and an organic solvent

[Chemical Formula 1]

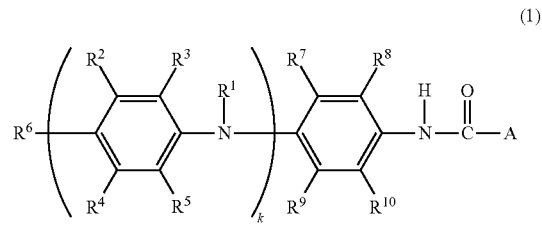

(1)

wherein R$^1$ is a hydrogen atom or alkyl group having 1 to 20 carbon atoms which may be substituted with Z, Z is a halogen atom, nitro group, cyano group, aldehyde group, hydroxy group, thiol group, sulfonic acid group, carboxyl group, an aryl group having 6 to 20 carbon atoms and which may be substituted with Z', or heteroaryl group having 2 to 20 carbon atoms which may be substituted with Z', and Z' is a halogen atom, nitro group, cyano group, aldehyde group, hydroxy group, thiol group, sulfonic acid group, or carboxyl group;

R$^2$ to R$^{10}$ are independently a hydrogen atom, halogen atom, nitro group, cyano group, or alkyl group having 1 to 20 carbon atoms, alkenyl group having 2 to 20 carbon atoms, alkynyl group having 2 to 20 carbon atoms, aryl group having 6 to 20 carbon atoms, or heteroaryl group having 2 to 20 carbon atoms which may be substituted with a halogen atom;

letter A is a fluoroalkyl group having 1 to 20 carbon atoms, fluorocycloalkyl group having 3 to 20 carbon atoms, fluorobicycloalkyl group having 4 to 20 carbon atoms, fluoroalkenyl group having 2 to 20 carbon atoms or fluroalkynyl group having 2 to 20 carbon atoms which may be substituted with a cyano group, chlorine atom, bromine atom, iodine atom, nitro group or fluoroalkoxy group having 1 to 20 carbon atoms, a fluoroaryl group having 6 to 20 carbon atoms which may be substituted with a cyano group, chlorine atom, bromine atom, iodine atom, nitro group, alkyl group having 1 to 20 carbon atoms, fluoroalkyl group having 1 to 20 carbon atoms or fluoroalkoxy group having 1 to 20 carbon atoms, an aryl group having 6 to 20 carbon atoms which is substituted with a fluoroalkyl group having 1 to 20 carbon atoms, fluorocycloalkyl group having 3 to 20 carbon atoms, fluorobicycloalkyl group having 4 to 20 carbon atoms, fluoroalkenyl group having 2 to 20 carbon atoms or fluoroalkynyl group having 2 to 20 carbon atoms, and may be substituted with a cyano group, halogen atom or fluoroalkoxy group having 1 to 20 carbon atoms, a fluoroaralkyl group having 7 to 20 carbon atoms which may be substituted with a cyano group, chlorine atom, bromine atom, iodine atom, nitro group, fluoroalkoxy group having 1 to 20 carbon atoms, fluoroalkyl group having 1 to 20 carbon atoms, fluorocycloalkyl group having 3 to 20 carbon atoms, fluorobicycloalkyl group having 4 to 20 carbon atoms, fluoroalkenyl group having 2 to 20 carbon atoms or fluoroalkynyl group having 2 to 20 carbon atoms, or an aralkyl group having 7 to 20 carbon atoms which is substituted with a fluoroalkyl group having 1 to 20 carbon atoms, fluorocycloalkyl group having 3 to 20 carbon atoms, fluorobicycloalkyl group having 4 to 20 carbon atoms, fluoroalkenyl group having 2 to 20 carbon atoms or fluoroalkynyl group having 2 to 20 carbon atoms, and may be substituted with a cyano group, halogen atom or fluoroalkoxy group having 1 to 20 carbon atoms; and letter k is an integer of 1 to 20.

2. The charge-transporting varnish of claim 1, wherein letter A is a fluoroalkyl group having 1 to 20 carbon atoms which may be substituted with a cyano group, chlorine atom, bromine atom, iodine atom, nitro group or fluoroalkoxy group having 1 to 20 carbon atoms; a fluoroaryl group having 6 to 20 carbon atoms which may be substituted with a cyano group, chlorine atom, bromine atom, iodine atom, nitro group, alkyl group having 1 to 20 carbon atoms, fluoroalkyl group having 1 to 20 carbon atoms or fluoroalkoxy group having 1 to 20 carbon atoms; or an aryl group having 6 to 20 carbon atoms is substituted with a fluoroalkyl group having 1 to 20 carbon atoms, fluorocycloalkyl group having 3 to 20 carbon atoms, fluorobicycloalkyl group having 4 to 20 carbon atoms, fluoroalkenyl group having 2 to 20 carbon atoms or fluoroalkynyl group having 2 to 20 carbon atoms, and may be substituted with a cyano group, halogen atom, or fluoroalkoxy group having 1 to 20 carbon atoms.

3. The charge-transporting varnish of claim 2, wherein letter A is a phenyl group which is substituted with at least 3 fluorine atoms, and may be substituted with a cyano group, chlorine atom, bromine atom, iodine atom, nitro group, alkyl group having 1 to 20 carbon atoms, fluoroalkyl group having 1 to 20 carbon atoms or fluoroalkoxy group having 1 to 20 carbon atoms; or a phenyl group which is substituted with a fluorocycloalkyl group having 3 to 20 carbon atoms, fluorobicycloalkyl group having 4 to 20 carbon atoms, fluoroalkenyl group having 2 to 20 carbon atoms, or fluoroalkynyl group having 2 to 20 carbon atoms, and may be substituted with a cyano group, halogen atom, or fluoroalkoxy group having 1 to 20 carbon atoms.

4. The charge-transporting varnish of any one of claims 1 to 3, wherein $R^1$ is a hydrogen atom.

5. The charge-transporting varnish of claim 1, wherein $R^2$ to $R^{10}$ are a hydrogen atom.

6. The charge-transporting varnish of claim 1, wherein letter k is an integer of 2 to 10.

7. The charge-transporting varnish of claim 1, wherein the fluorine-free charge-transporting substance is a compound represented by the formula (4) below:

aryl group having 6 to 20 carbon atoms or heteroaryl group having 2 to 20 carbon atoms which may be substituted with $Z^{12}$;

$R^{17}$ and $R^{18}$ are independently a hydrogen atom, halogen atom, nitro group, cyano group, amino group, aldehyde group, hydroxy group, thiol group, sulfonic acid group, carboxyl group, or alkyl group having 1 to 20 carbon atoms, alkenyl group having 2 to 20 carbon atoms or alkynyl group having 2 to 20 carbon atoms which may be substituted with $Z^{11}$, or aryl group having 6 to 20 carbon atoms or heteroaryl group having 2 to 20 carbon atoms which may be substituted with $Z^{12}$, or —$NHY^2$, —$NY^3Y^4$, —$C(O)Y^5$, —$OY^6$, —$SY^7$, —$SO_3Y^8$, —$C(O)OY^9$, —$OC(O)Y^{10}$, —$C(O)NHY^{11}$ or —$C(O)NY^{12}Y^{13}$;

$R^{11}$ to $R^{16}$ are independently a hydrogen atom, halogen atom, nitro group, cyano group, amino group, aldehyde group, hydroxy group, thiol group, sulfonic acid group, carboxyl group, or alkyl group having 1 to 20 carbon atoms, alkenyl group having 2 to 20 carbon atoms or alkynyl group having 2 to 20 carbon atoms which may be substituted with $Z^{11}$, or aryl group having 6 to 20 carbon atoms or heteroaryl group having 2 to 20 carbon atoms which may be substituted with $Z^{12}$, or —$NHY^2$, —$NY^3Y^4$, —$C(O)Y^5$, —$OY^6$, —$SY^7$, —$SO_3Y^8$, —$C(O)OY^9$, —$OC(O)Y^{10}$, —$C(O)NHY^{11}$ or —$C(O)NY^{12}Y^{13}$;

$Y^2$ to $Y^{13}$ are independently alkyl group having 1 to 20 carbon atoms, alkenyl group having 2 to 20 carbon atoms or alkynyl group having 2 to 20 carbon atoms which may be substituted with $Z^{11}$, or aryl group having 6 to 20 carbon atoms or heteroaryl group having 2 to 20 carbon atoms which may be substituted with $Z^{12}$;

$Z^{11}$ is a halogen atom, nitro group, cyano group, amino group, aldehyde group, hydroxy group, thiol group, sulfonic acid group, carboxyl group, or aryl group having 6 to 20 carbon atoms or heteroaryl group having 2 to 20 carbon atoms which has an optional substituent of $Z^{13}$;

$Z^{12}$ is a halogen atom, nitro group, cyano group, amino group, aldehyde group, hydroxy group, thiol group, sulfonic acid group, carboxyl group, or alkyl group having 1 to 20 carbon atoms, alkenyl group having 2 to 20 carbon atoms or alkynyl group having 2 to 20 carbon atoms which may be substituted with $Z^{13}$;

[Chemical Formula 2]

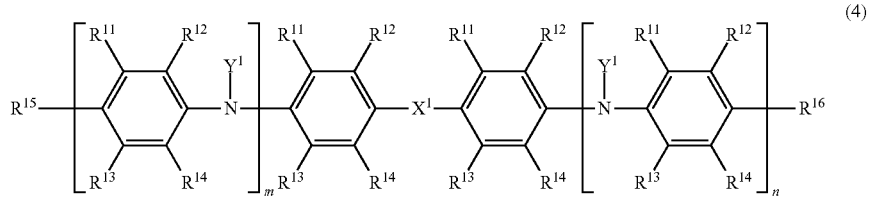

(4)

wherein $X^1$ is —$NY^1$—, —O—, —S—, —$(CR^{17}R^{18})_L$—, or a single bond, except that it is —$NY^1$— when m or n is 0;

$Y^1$ is independently a hydrogen atom, or alkyl group having 1 to 20 carbon atoms, alkenyl group having 2 to 20 carbon atoms or alkynyl group having 2 to 20 carbon atoms which may be substituted with $Z^{11}$, or $Z^{13}$ is a halogen atom, nitro group, cyano group, amino group, aldehyde group, hydroxy group, thiol group, sulfonic acid group, or carboxyl group; and letters of m and n are independently an integer at least 0, such that $1 \leq m+n \leq 20$.

8. The charge-transporting varnish of claim 1, further comprising a dopant.

9. A charge-transporting thin film which is produced from the charge-transporting varnish of claim 1.

10. An organic electroluminescent device comprising the charge-transporting thin film of claim 9.

* * * * *